(12) United States Patent
Schraga

(10) Patent No.: US 8,951,228 B2
(45) Date of Patent: Feb. 10, 2015

(54) IV INFUSION SYSTEM DEVICE HAVING RETRACTABLE NEEDLE AND METHOD OF MAKING AND USING THE SAME

(75) Inventor: Steven Schraga, Surfside, FL (US)

(73) Assignee: STAT Medical Devices, Inc., North Miami Beach, FL (US)

( * ) Notice: Subject to any disclaimer, the term of this patent is extended or adjusted under 35 U.S.C. 154(b) by 421 days.

(21) Appl. No.: 12/722,256

(22) Filed: Mar. 11, 2010

(65) Prior Publication Data

US 2011/0009873 A1 Jan. 13, 2011

Related U.S. Application Data

(60) Provisional application No. 61/159,635, filed on Mar. 12, 2009.

(51) Int. Cl.
| | | |
|---|---|---|
| *A61M 5/178* | (2006.01) | |
| *A61M 5/158* | (2006.01) | |
| *A61M 25/06* | (2006.01) | |
| *A61B 19/00* | (2006.01) | |
| *A61M 5/32* | (2006.01) | |
| *A61M 39/06* | (2006.01) | |

(52) U.S. Cl.
CPC ........... *A61M 5/158* (2013.01); *A61M 25/0631* (2013.01); *A61B 2019/481* (2013.01); *A61M 5/3257* (2013.01); *A61M 25/0637* (2013.01); *A61M 39/06* (2013.01); *A61M 2005/1585* (2013.01); *A61M 2005/1587* (2013.01)
USPC .................. 604/164.01; 604/164.12

(58) Field of Classification Search
USPC ................ 604/164.01, 164.12, 110; 606/108; 600/576
See application file for complete search history.

(56) References Cited

U.S. PATENT DOCUMENTS

| | | |
|---|---|---|
| 4,650,468 A | 3/1987 | Jennings, Jr. et al. |
| 4,929,238 A | 5/1990 | Baum |
| 5,002,533 A | 3/1991 | Jullien |
| 5,098,402 A | 3/1992 | Davis |
| 5,188,599 A | 2/1993 | Botich et al. |
| 5,188,600 A | 2/1993 | Jullien |
| 5,308,329 A | 5/1994 | Mazur et al. |
| 5,328,475 A | 7/1994 | Chen |
| 5,336,198 A | 8/1994 | Silver et al. |
| 5,344,403 A | 9/1994 | Lee |
| 5,569,203 A | 10/1996 | Chen |

(Continued)

FOREIGN PATENT DOCUMENTS

| | | |
|---|---|---|
| GB | 2 266 667 | 11/1993 |
| KR | 10-2004-0101698 | 12/2004 |
| WO | WO 9103269 A1 * | 3/1991 |

*Primary Examiner* — Theodore Stigell
(74) *Attorney, Agent, or Firm* — Greenblum & Bernstein, P.L.C.

(57) ABSTRACT

Device for installing and/or injecting a cannula includes a body, a needle holding member arranged in the body and comprising a needle, and a spring structured and arranged to move the needle holding member to a retracted position within the body. At least one of the spring is pre-tensioned or expanded and the spring is arranged on a side of the needle holding member opposite the needle. A method of using the device includes injecting insertion cannula to a skin surface and causing the needle holding member to retract into the body. A method of making the device includes placing the spring in an pre-tensioned or expanded position inside the body and connecting one end of the spring to the needle holding member. This Abstract is not intended to define the invention disclosed in the specification, nor intended to limit the scope of the invention in any way.

23 Claims, 41 Drawing Sheets

(56) References Cited

U.S. PATENT DOCUMENTS

| | | | |
|---|---|---|---|
| 5,591,131 A | 1/1997 | Chen | |
| 5,746,215 A | 5/1998 | Manjarrez | |
| 5,814,017 A | 9/1998 | Kashmer | |
| 5,858,000 A | 1/1999 | Novacek et al. | |
| 5,997,507 A * | 12/1999 | Dysarz | 604/161 |
| 6,074,373 A | 6/2000 | Sudo et al. | |
| 6,090,078 A * | 7/2000 | Erskine | 604/198 |
| 6,461,328 B2 | 10/2002 | Wang et al. | |
| 6,638,254 B2 * | 10/2003 | Nakagami | 604/164.08 |
| 6,641,555 B1 * | 11/2003 | Botich et al. | 604/110 |
| 6,648,849 B2 | 11/2003 | Tenhuisen et al. | |
| 6,835,190 B2 | 12/2004 | Nguyen | |
| 7,018,344 B2 | 3/2006 | Bressler et al. | |
| 7,037,292 B2 | 5/2006 | Carlyon et al. | |
| 7,097,633 B2 | 8/2006 | Botich et al. | |
| 7,294,118 B2 | 11/2007 | Saulenas et al. | |
| 2004/0254529 A1 | 12/2004 | Fitzgerald | |
| 2006/0084913 A1 | 4/2006 | Lo | |
| 2008/0154212 A1 | 6/2008 | Schraga | |
| 2008/0262421 A1 | 10/2008 | Schraga | |
| 2009/0069750 A1 | 3/2009 | Schraga | |

* cited by examiner

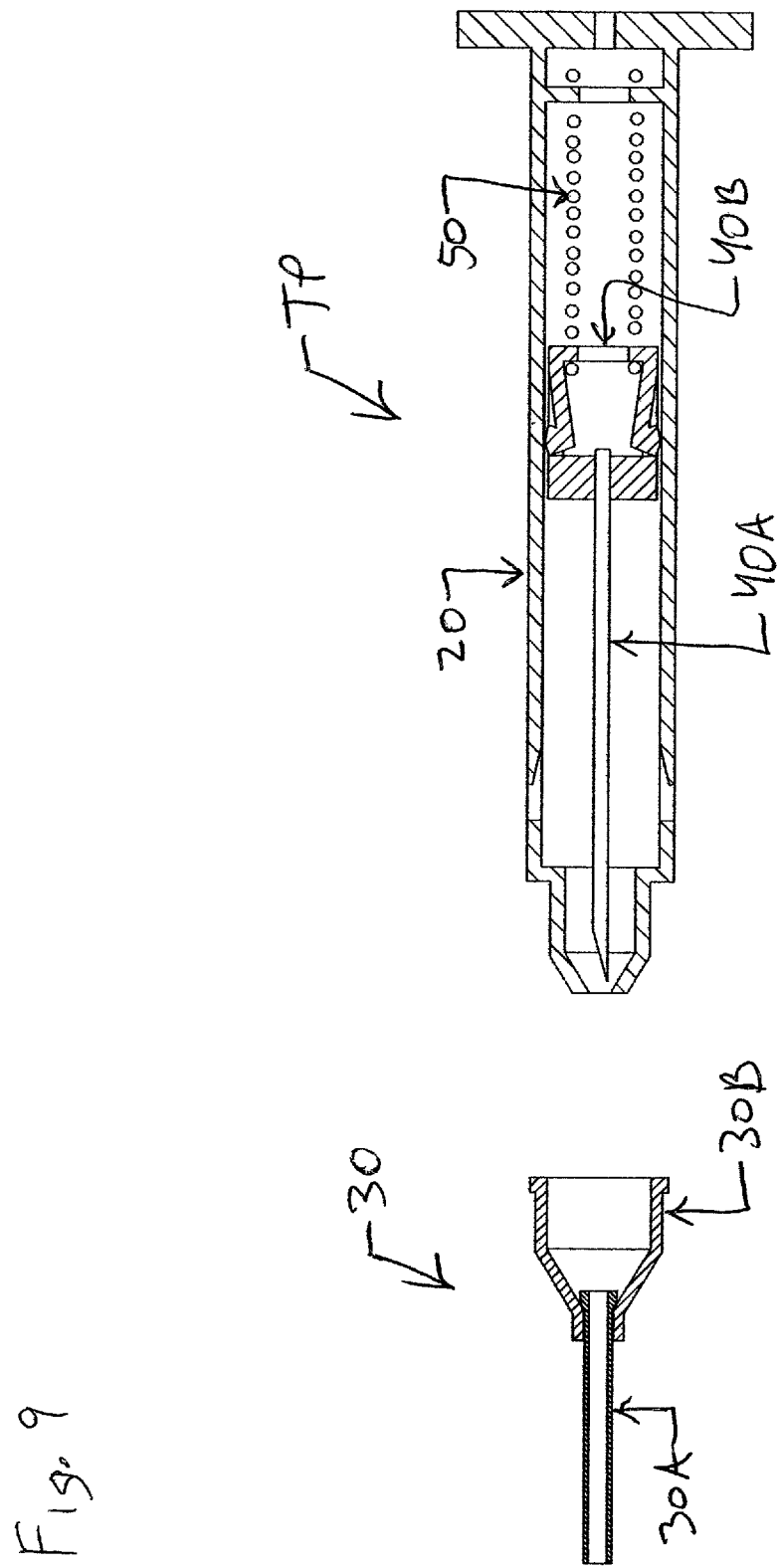

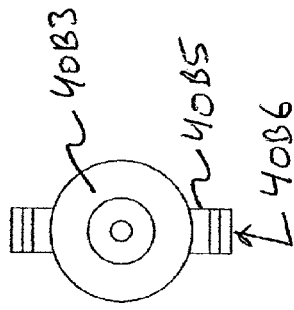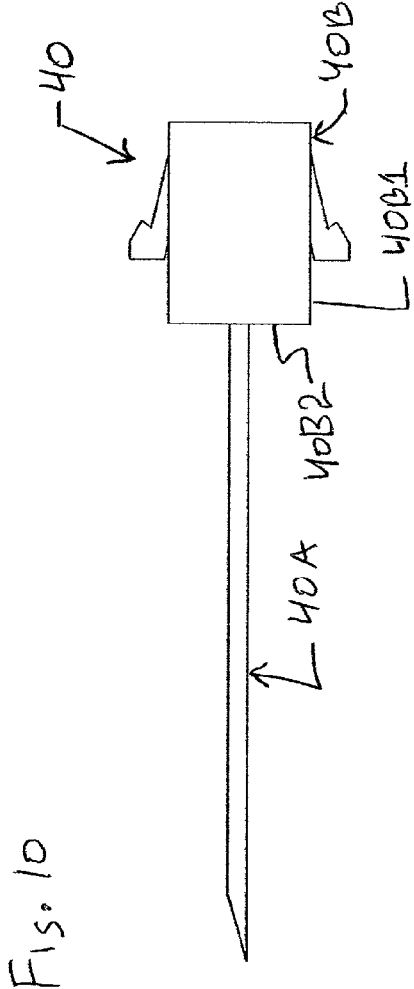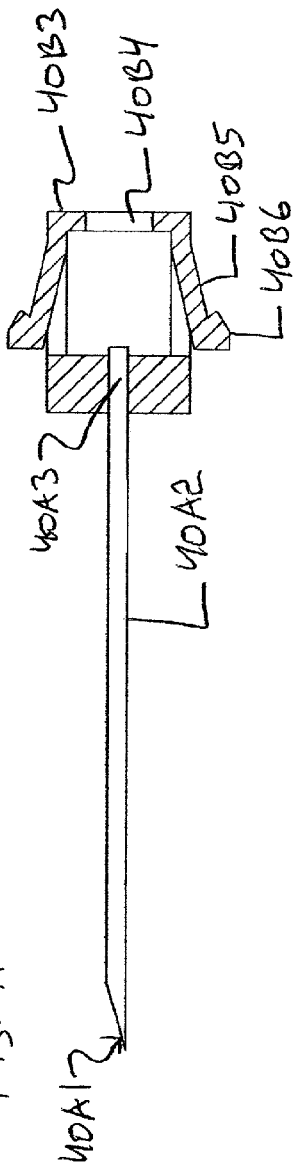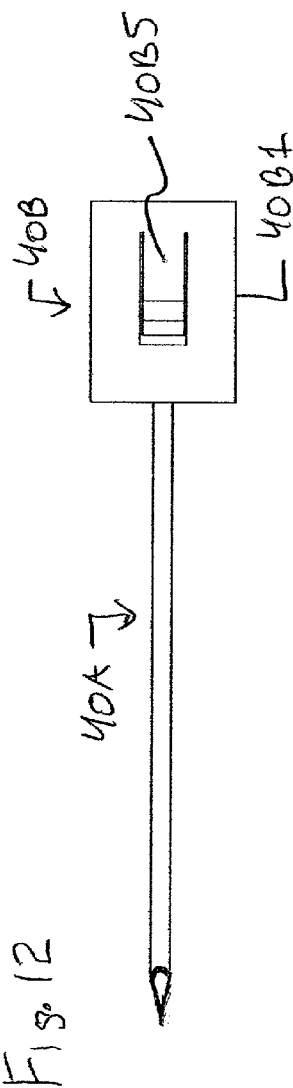

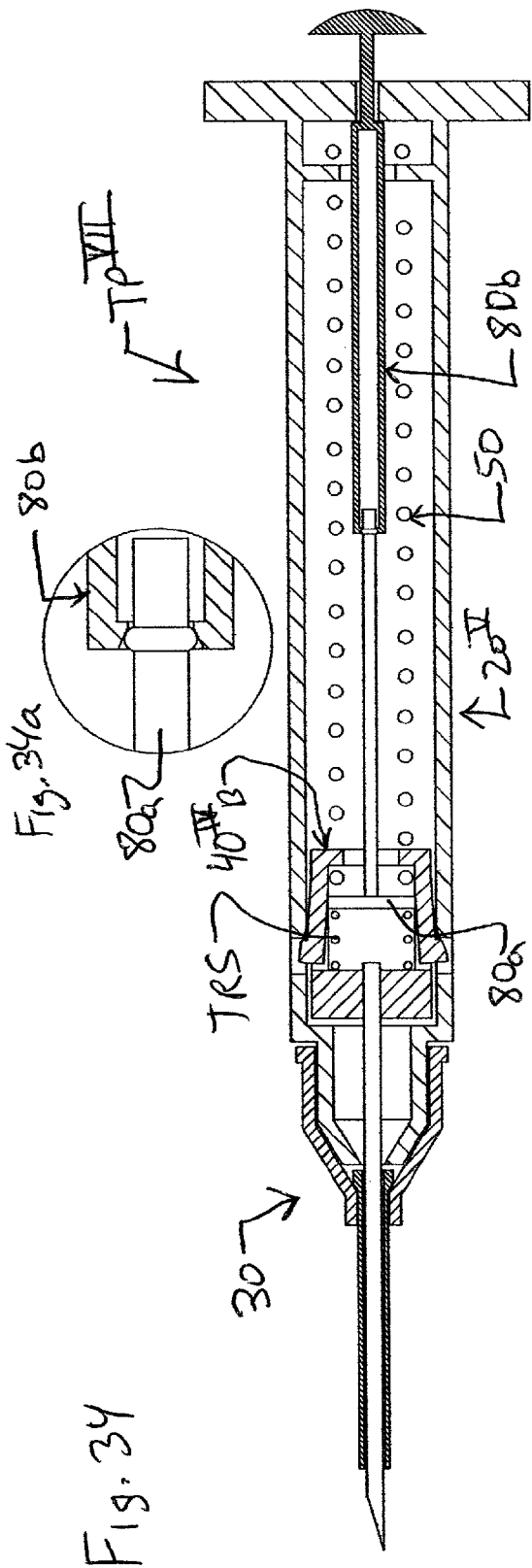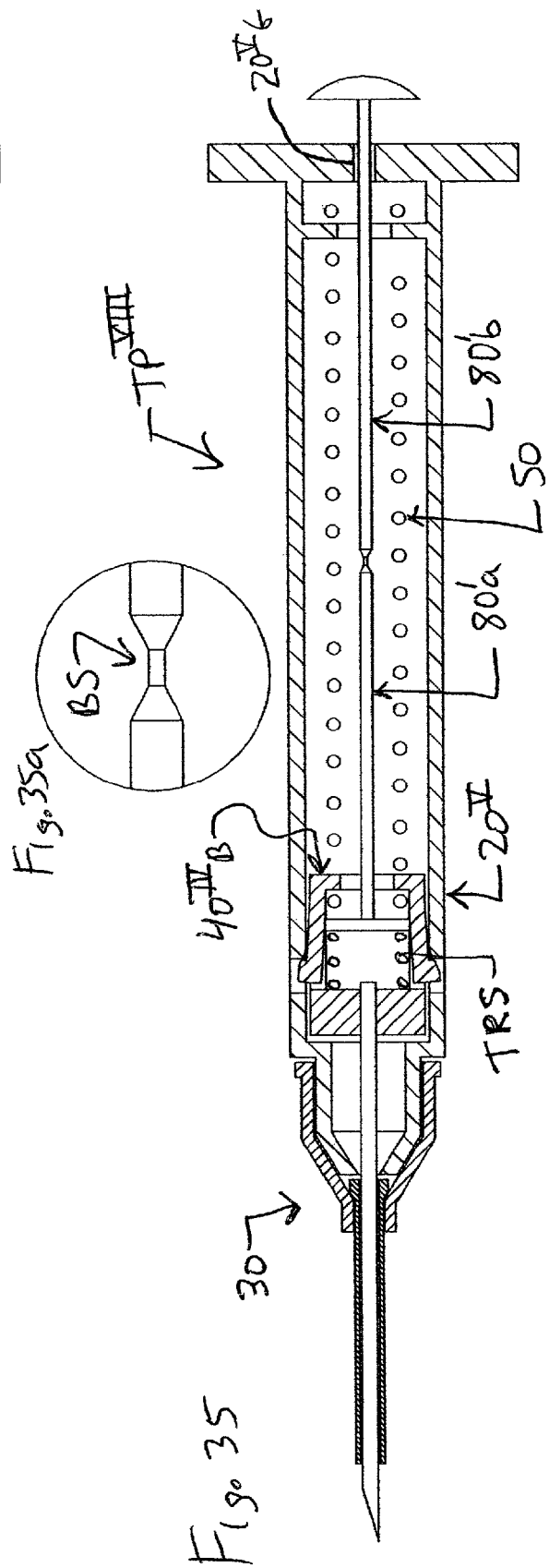

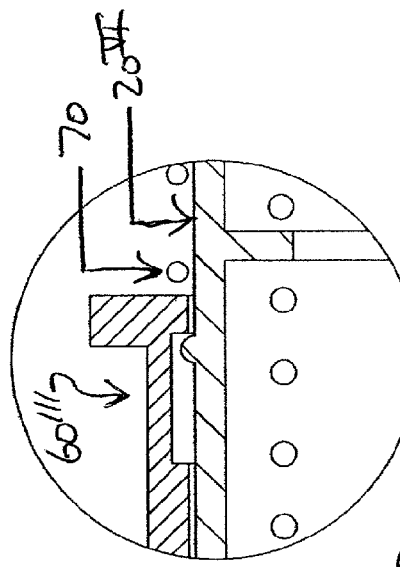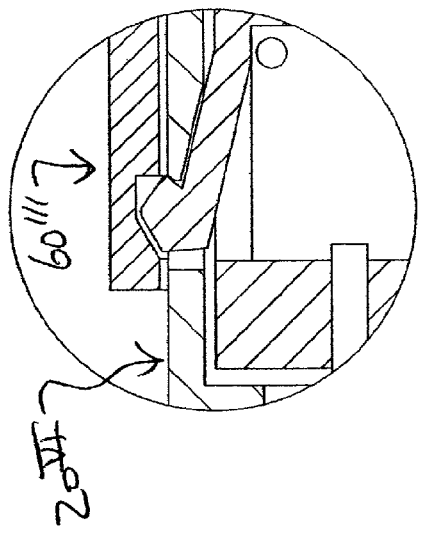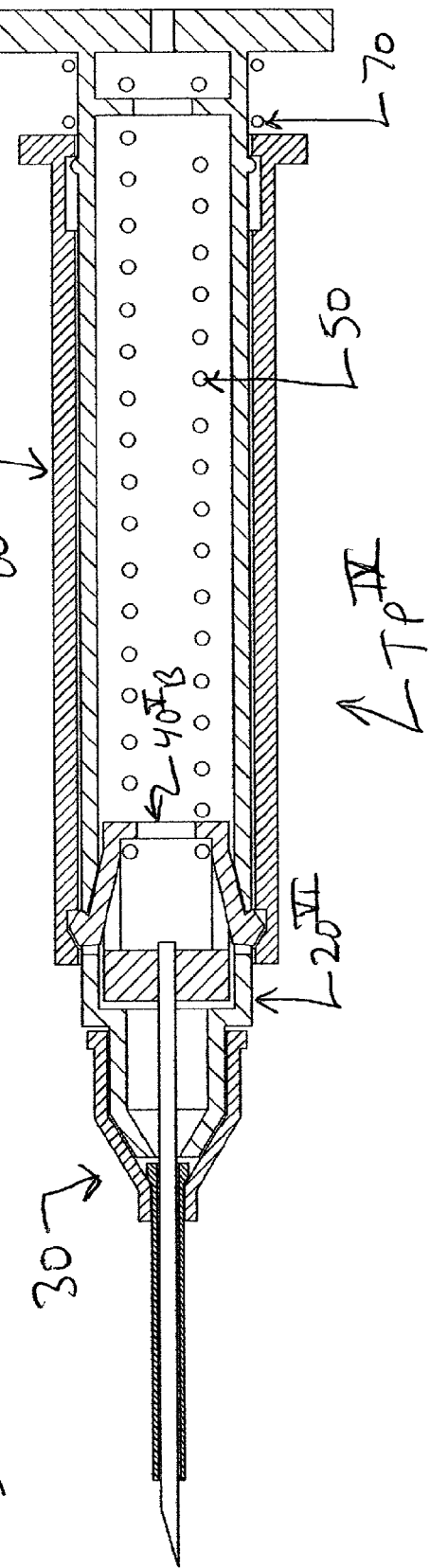
Fig. 36b
Fig. 36a
Fig. 36

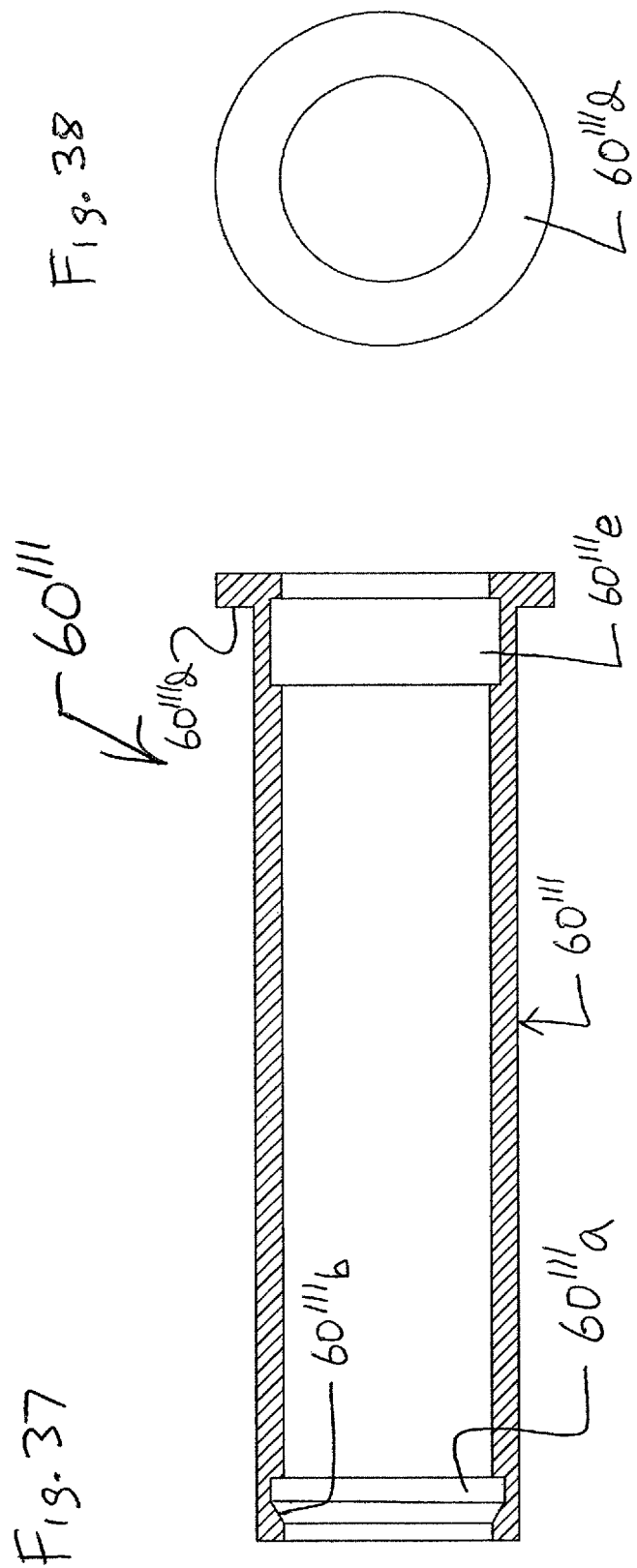

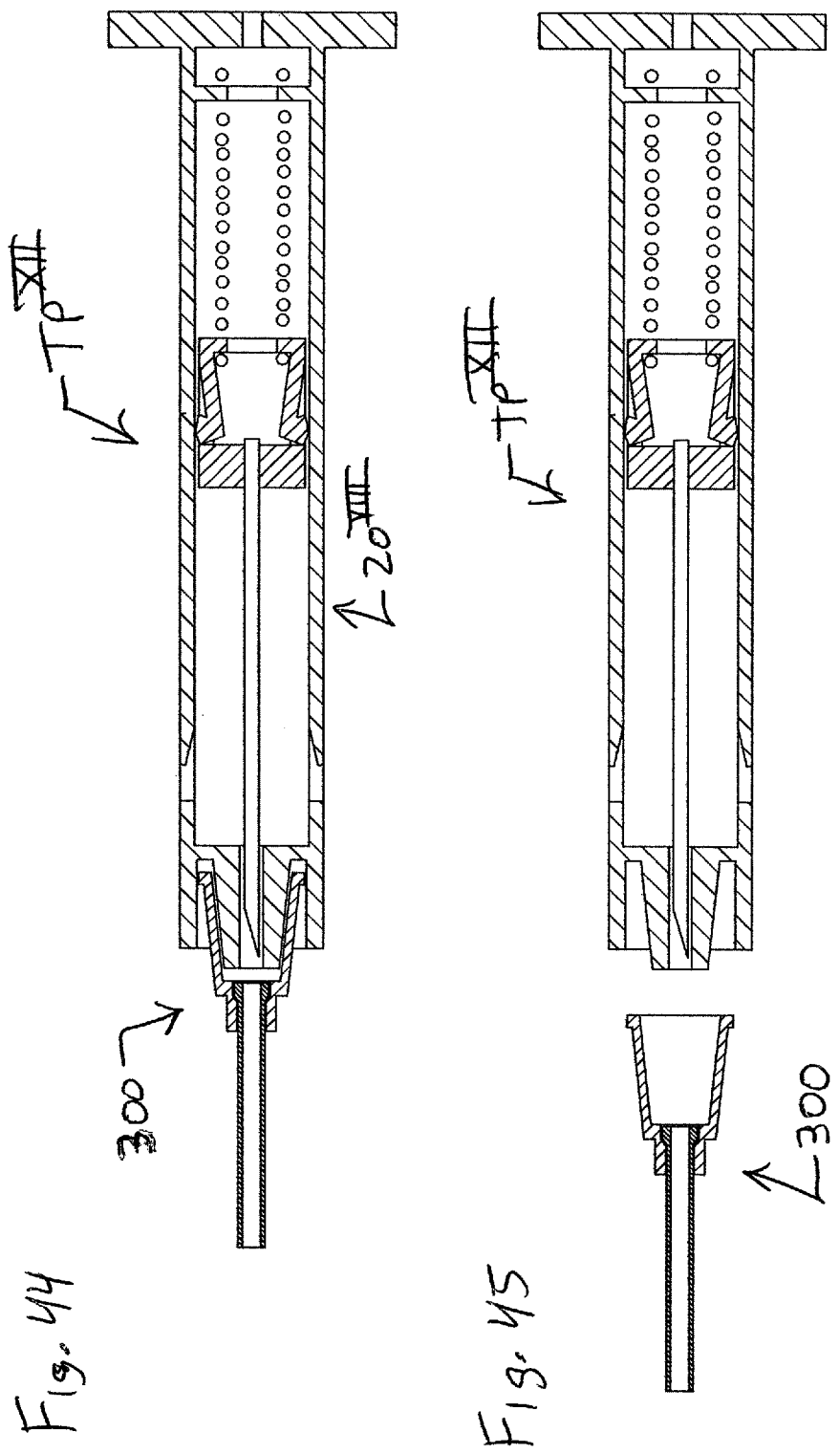

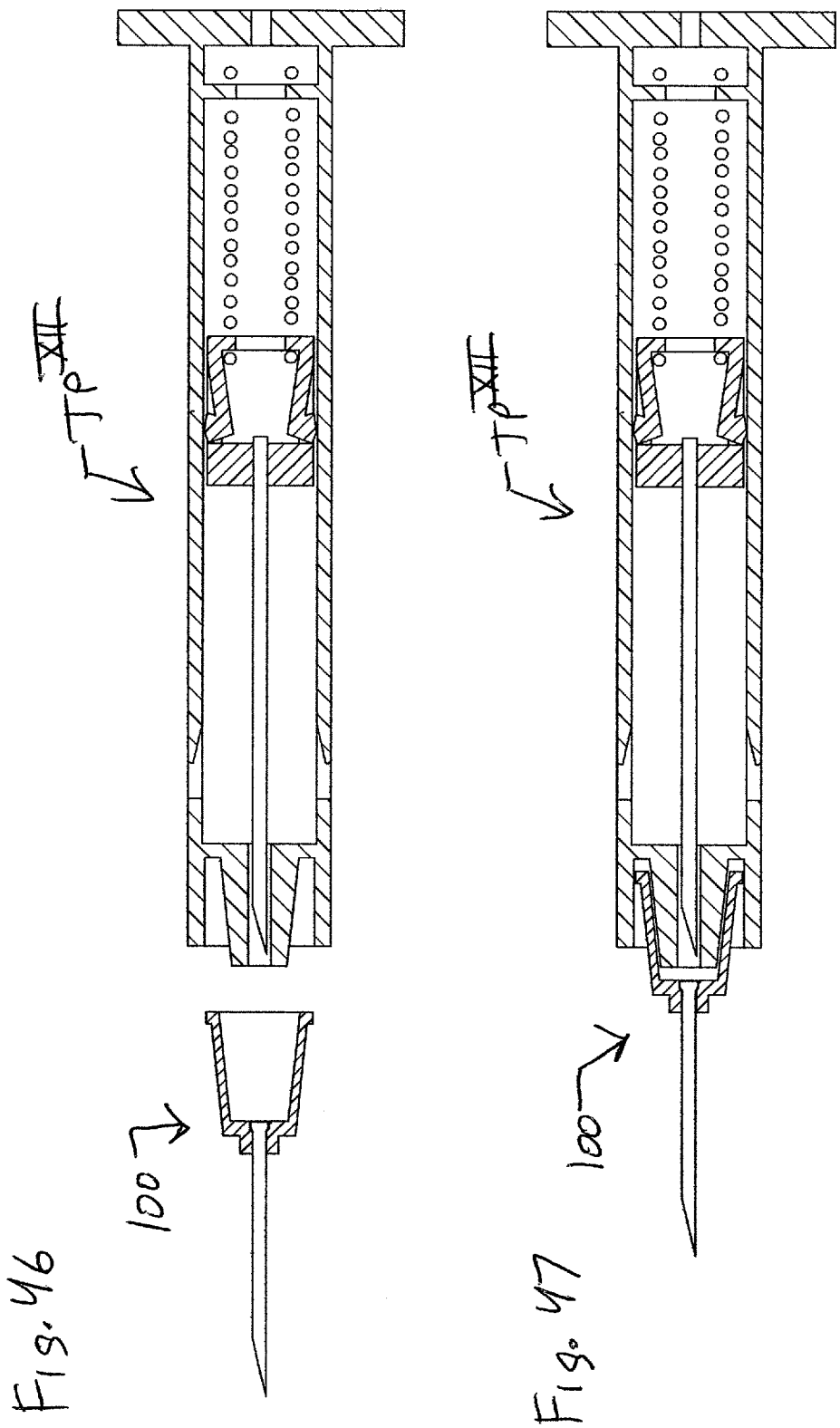

IV INFUSION SYSTEM DEVICE HAVING RETRACTABLE NEEDLE AND METHOD OF MAKING AND USING THE SAME

CROSS-REFERENCE TO RELATED APPLICATIONS

The instant application is a US non-provisional Application based on U.S. provisional application No. 61/159,635, filed Mar. 12, 2009, the disclosure of which is hereby expressly incorporated by reference hereto in its entirety.

BACKGROUND OF THE INVENTION

1. Field of the Invention

The invention relates generally to devices used to collect fluid samples from, e.g., patients. More specifically, this invention relates to an IV infusion device having a retractable needle. The invention also relates to a tool for installing and/or injecting an IV collection tip. The tip can be used to deliver drugs into, e.g., a patient. The tool can be a single-use and/or disposable tool. The invention also relates to a method of collecting a fluid sample with the device as well as a method of making the device. The invention also relates to a blood sample collection system that utilizes a device which can retract the insertion needle into the device.

2. Discussion of Background Information

The following relate to infusion devices: U.S. Pat. No. 6,090,078 to ERSKINE; U.S. Pat. No. 6,641,555 to BOTICH et al.; U.S. Pat. No. 5,746,215 to MANJARREZ; and U.S. Pat. No. 7,097,633 to BOTICH et al. The entire disclosure of each of these documents is hereby expressly incorporated by reference in their entireties. The invention provides improvements over such devices such as using a pre-tensioned spring to cause retraction of the insertion or puncturing needle.

SUMMARY OF THE INVENTION

According to one non-limiting aspect of the invention there is provided a device for installing and/or injecting a cannula comprising a body, a needle holding member arranged in the body and comprising a needle or cannula, and a spring structured and arranged to move the needle holding member to a retracted position within the body, wherein at least one of the spring is pre-tensioned or expanded and the spring is arranged on a side of the needle holding member opposite the needle or cannula.

According to one non-limiting aspect of the invention the device further comprises a cannula hub arranged on a front end of the body.

According to one non-limiting aspect of the invention the device further comprises a removable cannula hub arranged on a front end of the body.

According to one non-limiting aspect of the invention the device further comprises a device for triggering movement of the needle holding member.

According to one non-limiting aspect of the invention, there is provided a device for installing and/or injecting a cannula comprising a body, a removable cannula hub arranged on a front end of the body and comprising a insertion cannula, a needle holding member arranged in the body and comprising a needle or cannula sized and configured to extend into the insertion cannula, and a spring structured and arranged to move the needle holding member to a retracted position within the body, wherein at least one of the spring is pre-tensioned or expanded and the spring is arranged on a side of the needle holding member opposite the needle or cannula.

According to one non-limiting aspect of the invention, there is provided a device for installing and/or injecting a cannula comprising a body, a removable cannula hub arranged on a front end of the body and comprising a insertion cannula, a needle holding member arranged in the body and comprising a needle or cannula sized and configured to extend into the insertion cannula, a device for allowing a user to trigger movement of the needle holding member, and a spring structured and arranged to move the needle holding member to a retracted position within the body, wherein at least one of the spring is pre-tensioned or expanded and the spring is arranged on a side of the needle holding member opposite the needle or cannula.

According to one non-limiting aspect of the invention, there is provided a device for installing and/or injecting a cannula comprising at least one feature disclosed in the instant application.

According to one non-limiting aspect of the invention, there is provided a method of using any one of the devices disclosed herein, the method comprising injecting insertion cannula to a skin surface and causing the needle holding member to retract into the body.

According to one non-limiting aspect of the invention, there is provided a method of making any one of the devices disclosed herein, the method comprising placing the spring in an pre-tensioned or expanded position inside the body and connecting one end of the spring to the needle holding member.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 9 shows the side cross-section view of FIG. 8 after the cannula portion is disconnected from the device body. Once disconnected, the cannula portion can remain injected into the skin while the body portion of the device can be removed and safely discarded with the puncturing needle safely retained and fully enclosed by the body of the device so as to prevent inadvertent pricking of those who might handle the body of the device;

FIG. 10 shows a side view of the puncturing needle/trigger hub member used on the device of FIG. 1;

FIG. 11 shows a side cross-section view of the puncturing needle/trigger hub member shown in FIG. 10;

FIG. 12 shows a side view of the puncturing needle/trigger hub member shown in FIG. 10, but rotated 90 degrees;

FIG. 13 shows a rear side view of the puncturing needle/trigger hub member shown in FIG. 10;

FIG. 17 shows the fluid collection device prior to being connected to the cannula portion. FIG. 18 shows the fluid collection device connected to the cannula portion. FIG. 19 shows the fluid collection device connected to the cannula portion and having a blood collection tube inserted therein;

In FIG. 32, the device is shown before triggering by axial movement of the trigger ring. In FIG. 33, the device is shown during triggering by axial movement of the trigger ring;

FIG. 34 shows a side cross-section view of still another non-limiting embodiment of the device with the protective cap removed. The device is shown in a ready-to-use configuration. This configuration is an injection configuration. In this embodiment, the device is triggered by axial movement of, i.e., by depressing, the rearward extending trigger button;

FIG. 34a shows an enlarged view of a triggering arrangement of the device of FIG. 34;

FIG. 35 shows a side cross-section view of still another non-limiting embodiment of the device with the protective cap removed. The device is shown in a ready-to-use configuration. This configuration is an injection configuration. In this embodiment, the device is triggered by axial movement of, i.e., by depressing, the rearward extending trigger button;

FIG. 35a shows an enlarged view of a breakable section forming the triggering arrangement of the device of FIG. 35;

FIG. 36 shows a side cross-section view of still another non-limiting embodiment of the device with the protective cap removed. The device is shown in a ready-to-use configuration. This configuration is an injection configuration. In this embodiment, the device is triggered by axial movement of a trigger sleeve against the biasing force of a trigger spring;

FIG. 36a shows an enlarged view of a triggering/retaining portion of the device of FIG. 36;

FIG. 36b shows an enlarged view of a rear portion of the triggering sleeve of the device of FIG. 36;

FIG. 37 shows a side cross-section view of the trigger sleeve used in the device of FIG. 36;

FIG. 38 shows a rear side view of the trigger sleeve shown in FIG. 37;

FIG. 44 shows the side cross-section view of another embodiment of the device according to the invention. The device is shown after triggering of the device. Unlike the device shown in FIG. 1, this device uses a luer lock type connection between the cannula portion and the body of the device;

FIG. 45 shows the side cross-section view of FIG. 44 after the cannula portion is disconnected from the device body. Once disconnected, the cannula portion can remain injected into the skin while the body portion of the device can be removed and safely discarded with the puncturing needle safely retained and fully enclosed by the body of the device so as to prevent inadvertent pricking of those who might handle the body of the device;

FIGS. 46 and 47 show side cross-section views of another embodiment of the device according to the invention. The device is shown after triggering of the device. Unlike the device shown in FIG. 45, this device can be used after it is utilized to install a cannula portion. FIG. 46 shows that the device being used again by connecting it to a different cannula portion. Since the puncturing needle remains safely disposed in the body, there is no danger of pricking by re-using the device;

DETAILED DESCRIPTION OF THE INVENTION

Figure 1:
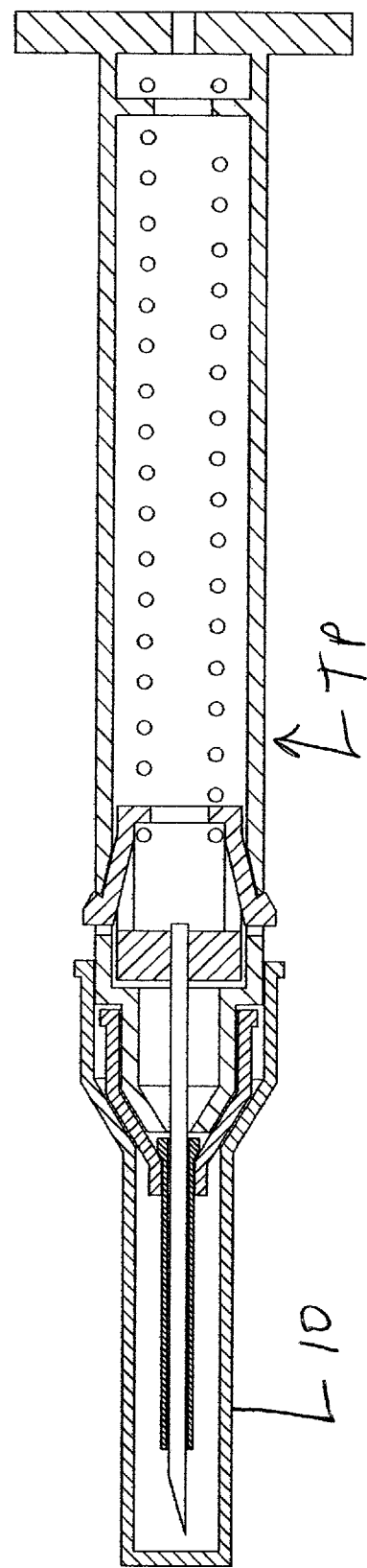
FIG. 1 shows a side cross-section view of a first non-limiting embodiment of the device according to the invention. The device is shown in an original prior-use and/or packaged configuration. The puncturing needle is not shown in cross-section.

Referring now to the drawings and first to FIGS. 1-15 which shows a first embodiment of a device for inserting a cannula member into skin. The tool or device includes three main parts; a tool portion TP, a removable safety or protective cap 10, and a cannula hub portion CHP.

Figure 4:
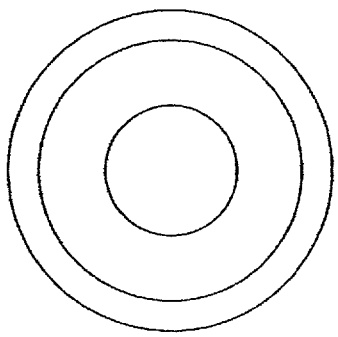
FIG. 4 shows a rear side view of the removable protective cap of FIG. 2.
Figure 2:
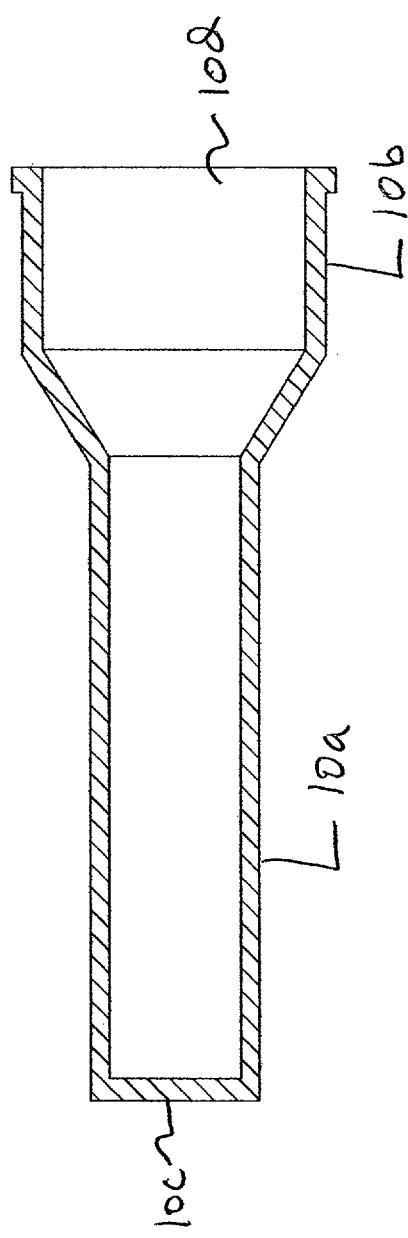
FIG. 2 shows a side cross-section view of a removable protective cap used on the device of FIG. 1.
Figure 3:
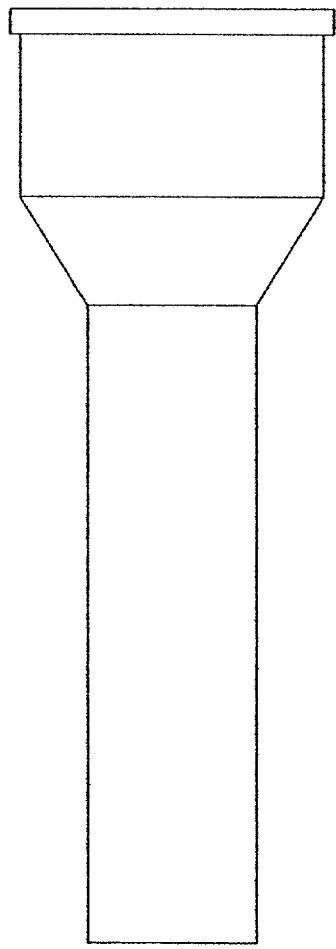
FIG. 3 shows a side view of the removable protective cap of FIG. 2.

The safety cap 10 is shown in FIGS. 2-4. The safety cap 10 includes a reduced diameter section 10*a* having a closed end 10*c* and an enlarged diameter section 10*b* whose internal generally cylindrical section 10*d* is sized and configured to frictionally engage with (when installed on) the front end section 20A (see FIGS. 14 and 15) of the body 20. The safety cap 10 protects the user from pricking him/her self when the device if removed from its package (not shown). By way of non-limiting example, the safety cap 10 can be made of a medical grade synthetic resin such as those typically utilized for syringes.

Figure 5:
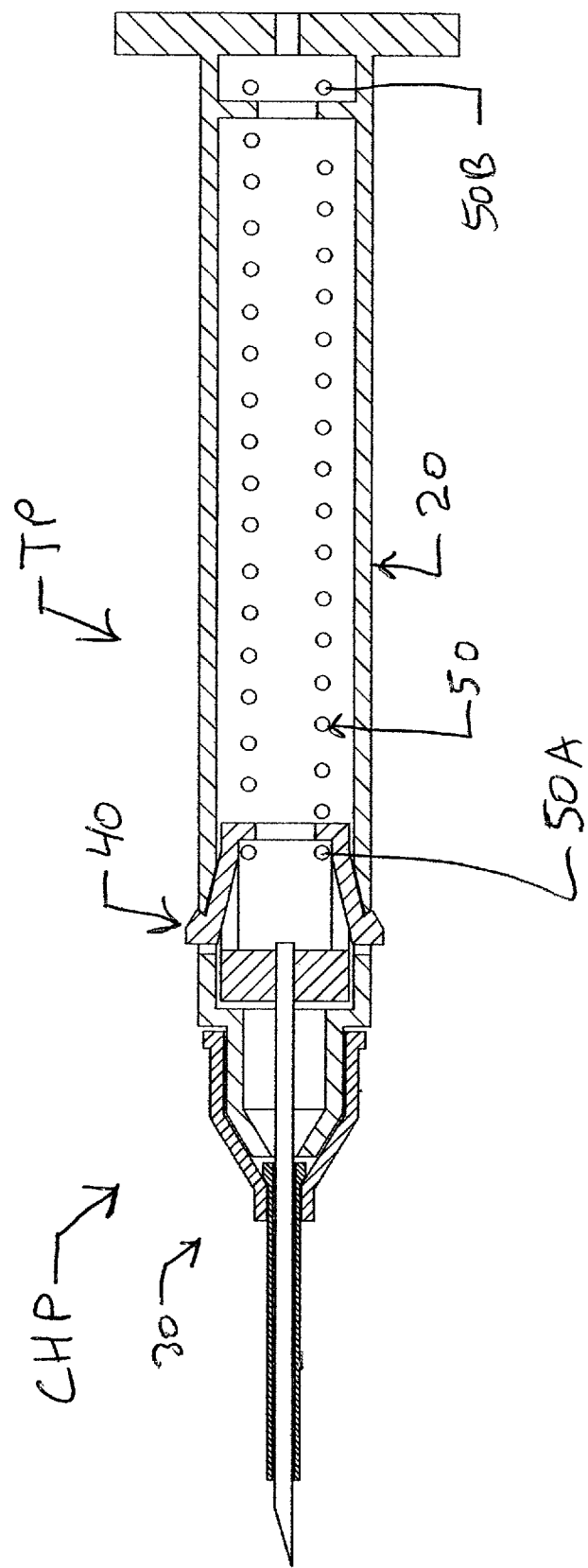
FIG. 5 shows a side cross-section view of the first non-limiting embodiment of FIG. 1 with the protective cap removed. The device is shown in a ready-to-use configuration. In this configuration, a user of the device may inject the device into the skin.

FIG. 5 shown the tool portion TP with the cannula member portion CHP installed thereon in the ready to use position. The safety cap 10 has been removed. As can be seen in FIG. 5, the cannula member portion CHP includes a cannula member 30. The tool portion TP includes a body 20, a puncturing needle member or needle hub 40, and a spring 50. The spring 50 has a front end 50A coupled to a rear end portion of the hub of the needle hub 40 and another end 50B coupled to an internal shoulder of the body 20. In the configuration shown in FIG. 5, the spring 50 is under tension and biases the needle hub 40 towards the rear end of the body 20.

Figure 6:
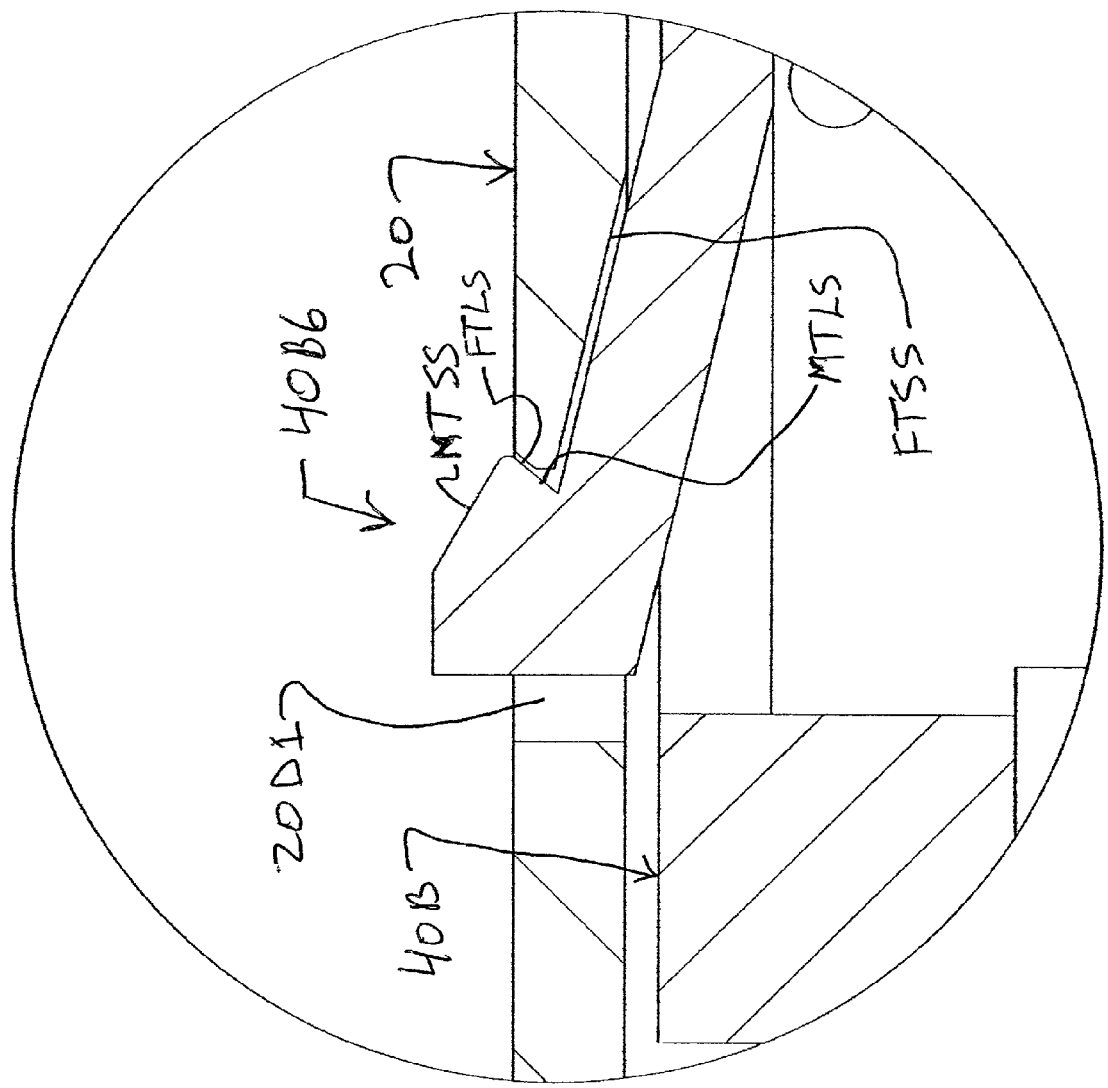
FIG. 6 shows an enlarged view of a triggering/retaining portion of the device of FIG. 5.
Figure 7:
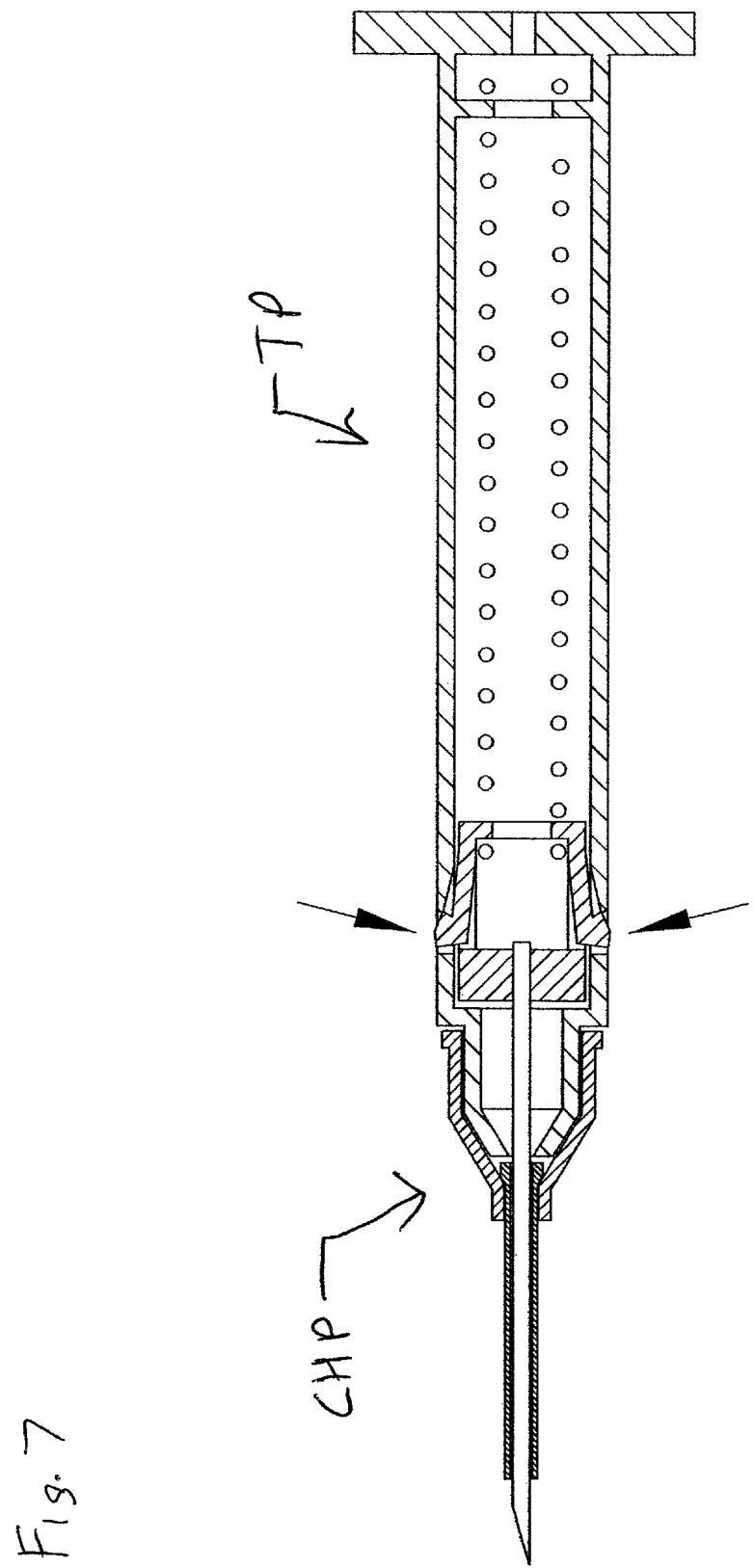
FIG. 7 shows the side cross-section view of FIG. 5 during a triggering of the device. Triggering occurs when a user applies the force indicated by arrows. The triggering typically occurs when the device is injected into the skin.
Figure 8:
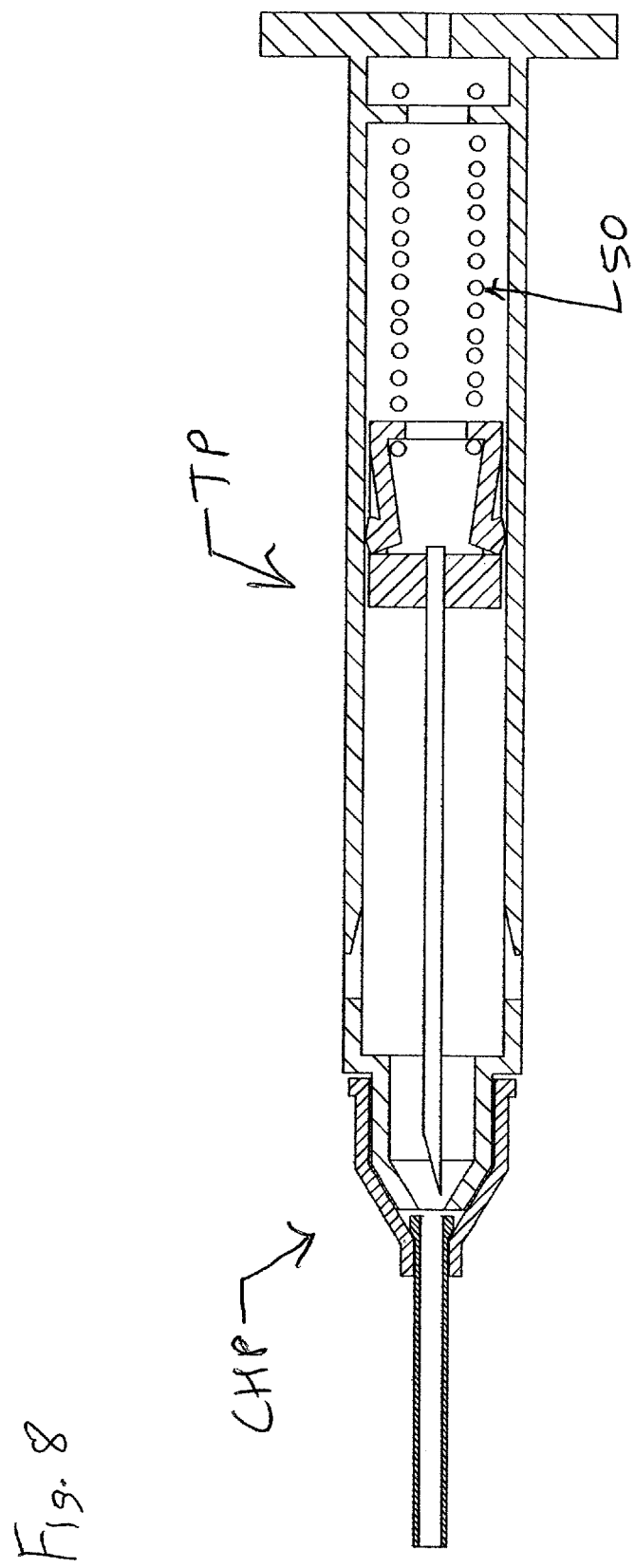
FIG. 8 shows the side cross-section view of FIG. 7 after triggering of the device. As is apparent, the spring which was in tension or axially expanded in FIG. 7 has assumed a relaxed or axially contracted stage thereby withdrawing the puncturing needle into the body of the device.

As can be seen in FIG. 6, oppositely arranged deflectable retaining members 40B6 of the needle hub 40 engage with openings 20D1 of the body 20 so as to retain the needle hub 40 in the position shown in FIG. 5. To ensure the each deflectable retaining members 40B6 of the needle hub 40 remains engaged with opening 20D1 of the body 20, each deflectable retaining member 40B6 has a movable tapered locking surface MTLS which engages with a fixed tapered locking surface FTLS. During triggering of the device TR, each deflectable retaining member 40B6 is moved inwardly so as to cause disengagement of the movable tapered locking surface MTLS from the fixed tapered locking surface FTLS, as shown in FIG. 7. Triggering occurs in FIG. 7 when a user applied a force (indicated by arrows) to each deflecting member 40B6 sufficient to allow disengagement between surfaces MTLS and FTLS. This can occur by the user applying these forces with the thumb and forefinger. When the device TP is triggered, the movable tapered sliding surface MTSS will slidably engage with the fixed tapered sliding surface FTSS (causing more inward deflection of the members 40B6) as the spring 50 moves the needle hub 40 to the fully retracted or withdrawn position shown in FIG. 8.

FIG. 9 shows how the cannula portion 30 can be disconnected from the device TR. Once disconnected, the cannula portion 30 can remain injected into the skin while the device TP can be removed and safely discarded with the puncturing member 40 (and especially the needle 40A) safely retained and fully enclosed by the body 20 of the device TP so as to prevent inadvertent pricking of those who might handle the device TR. The cannula member 30 can be of any conventionally known type such as those used for, e.g., used for IV infusion. In embodiments, the cannula member 30 includes at least a hollow needle portion 30A and a hub portion 30B.

FIGS. 10-13 show the needle hub or puncturing needle member 40 includes at least a needle portion 40A and a hub portion 40B. The hub portion 40B is, in embodiments, a generally cylindrical member and includes, in embodiments, two oppositely arranged deflectable retaining members 40B6 which function as described above. The generally cylindrical surface 40B1 is sized and configured to freely and slidably engage with an inner cylindrical surface of the body 20 as it moves within with space 20E (see FIG. 15). Each deflectable retaining member 40B6 is made deflectable by virtue of being coupled (or integrally formed with) a deflectable arm 40B5 whose opposite end is coupled (or integrally formed with) the hub 40B. The hub portion 40B also includes, in embodiments, a generally annular front surface 40B2, a generally annular rear surface 40B3, and an opening 40B4 which receives therein a portion of the spring 50 as described above. The deflectable retaining members 40B6/40B5 assume the position shown in FIGS. 10, 11 and 13 in the original/uninstalled/relaxed position. Once installed in the body 20 as shown in FIGS. 5 and 6, this ensures that they retain the needle hub 40 in the extended position and prevent the spring 50 from retracting the same fully into the device TP until triggering. The needle portion 40A includes a front puncturing end 40A1, a main shaft or body portion 40A2, and a rear end portion 40A3 which is fixedly secured to the hub 40B. The needle portion 40A can be of any conventionally known type such as those used for, e.g., used for IV infusion.

Figure 14:
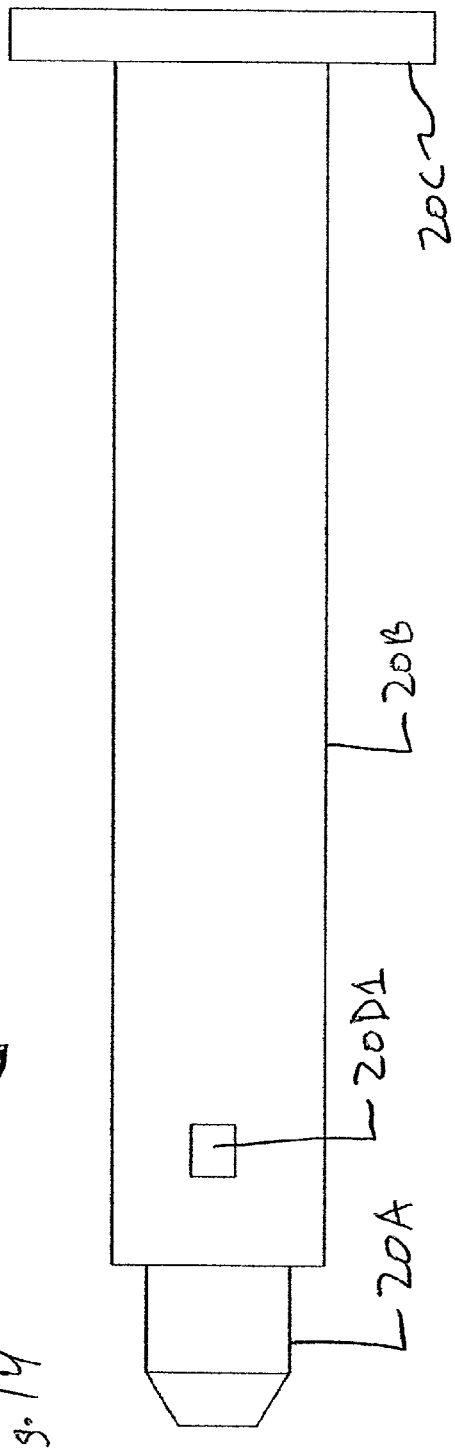
FIG. 14 shows a side view of the body used on the device of FIG. 1, but rotated 90 degrees.
Figure 15:
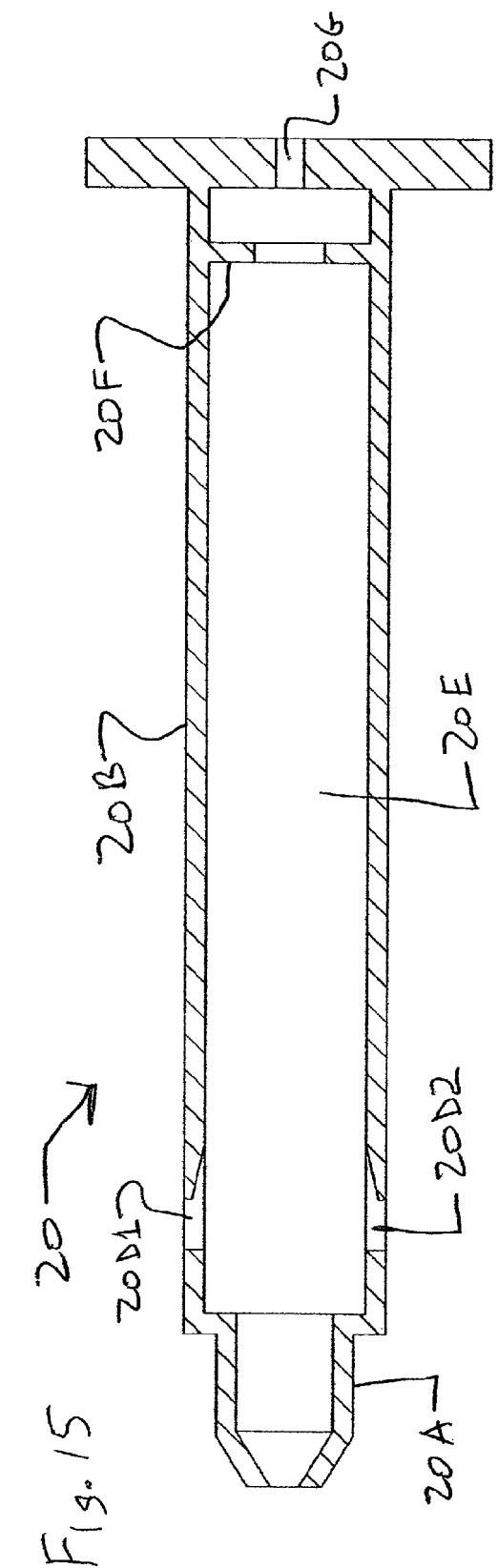
FIG. 15 shows a side cross-section view of the body of FIG. 14, but rotated 90 degrees back to the position shown in FIG. 1.

FIGS. 14 and 15 show the body 20 of the device TR. The body 20 includes a generally cylindrical cannula hum receiving section 20A, a main body portion 20B, and a rear flange 20C. The main body portion 20B is, in embodiments, a generally cylindrical member and includes, in embodiments, two oppositely arranged through openings 20D1 and 20D2 which are sized and configured to receive therein deflectable retaining members 40B6 which function as described above. A generally cylindrical space 20E arranged inside the body 20 and is sized and configured to receive therein the needle hub 40 and spring 50. A retaining flange 20F is arranged with the space 20E and in an area of the rear end of the body 20. A rear end of the spring 50 is coupled/secured to the flange 20F such that the flange 20F serves to anchor the non-movable end of the spring 50. A through opening 20G is disposed at a rear end of the body 20 in order to serve as a vent and to facilitate assembly of the device TR.

Figure 16:
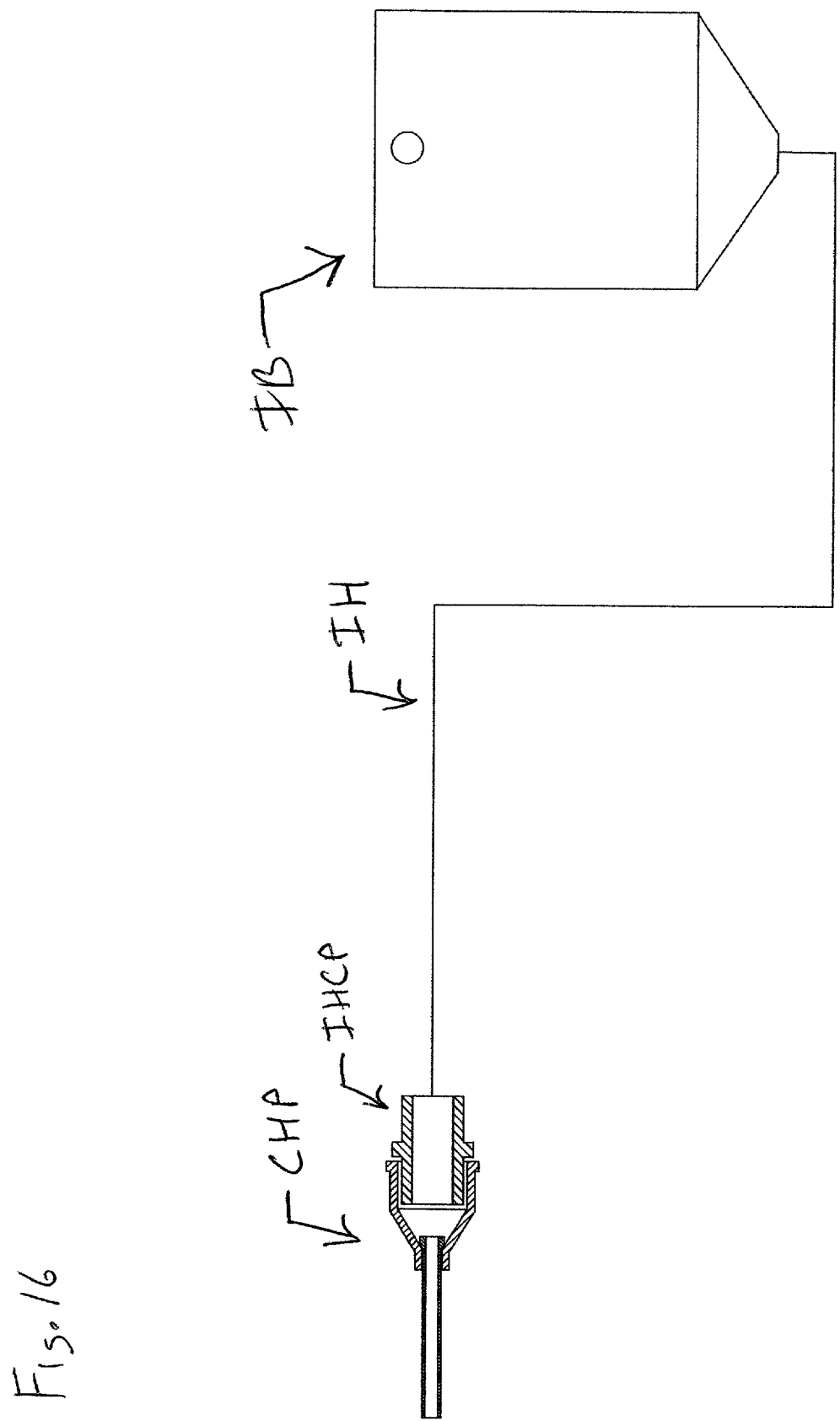
FIG. 16 shows the side cross-section view of the cannula portion connected to a connector and with the connector being coupled to a fluid containing and/or draining container via a conduit. With the cannula portion injected into the skin, fluid can be drained from or delivered into via the cannula portion. Although not shown, such a system preferably utilizes one or more valves or devices to ensure flow in only one desired direction.

FIG. 16 shows one non-limiting way in which the cannula portion CHP (whose cannula 30A has been previously injected into tissue) can be connected to a connector IHCP by, e.g., inserting one end of the connector IHCP into the hub 30B. Another end of the connector IHCP is coupled to a fluid containing and/or draining container IB, such as an IV infusion bag, via a conduit IH. With the cannula portion CHP injected into the skin, fluid can be drained from or delivered into the tissue via the cannula portion CHP. Although not shown, such a system preferably utilizes one or more valves or devices to ensure flow in only one desired direction. As such valves are well known, no additional details are herein provided.

Figure 17:
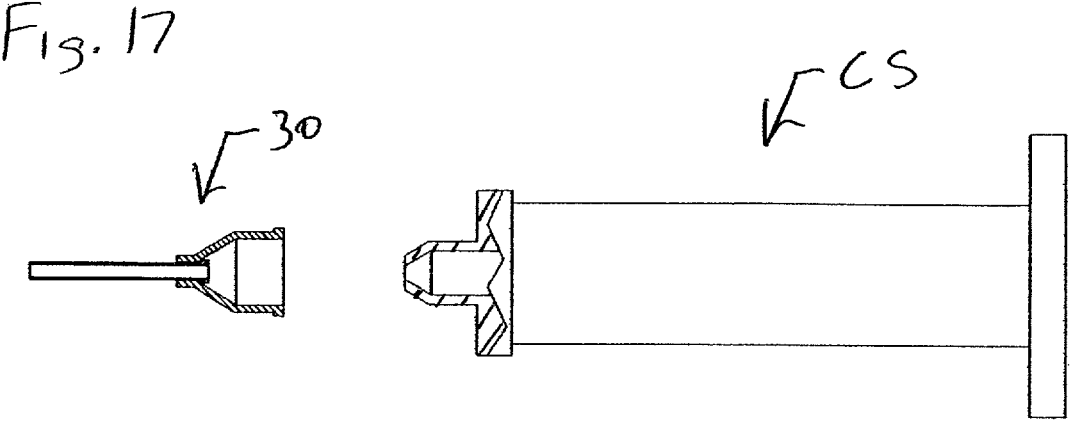
FIGS. 17-19 show side partial cross-section views of an embodiment of the device according to the invention in which the cannula portion (which in this embodiment would be in an injected state) can be connected to a fluid collection device such those that utilize a blood collection tube or vial or vacutainer type collection tube.
Figure 18:
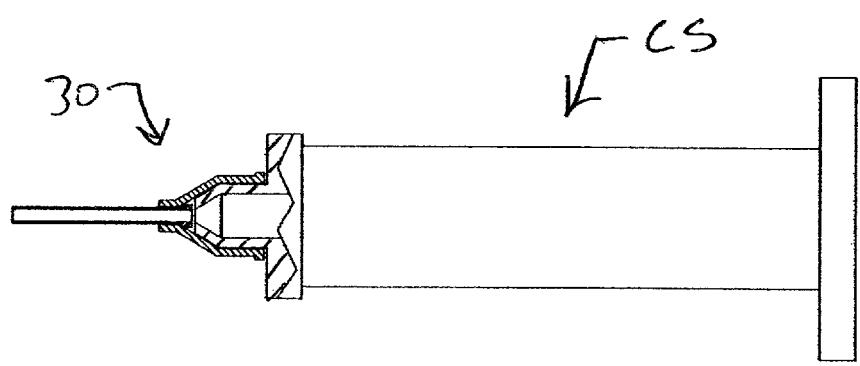
Figure 19:
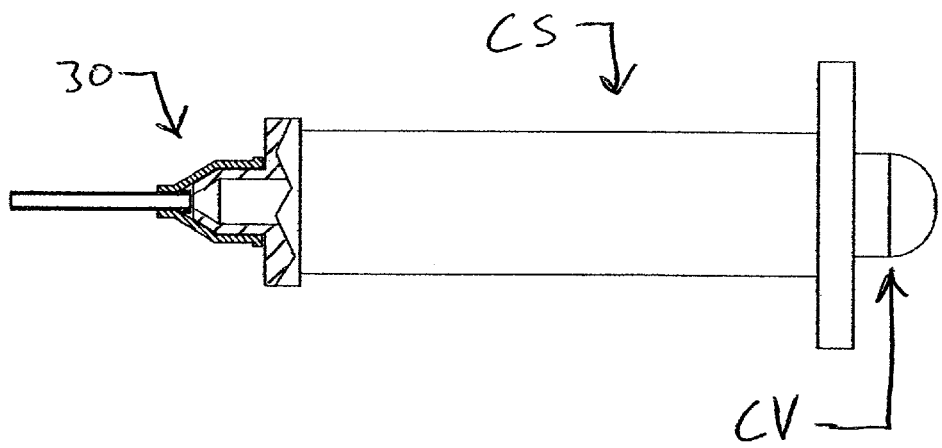

FIGS. 17-19 show one non-limiting way in which the cannula portion 30 can be used after the cannula portion 30 is injected into tissue via the device TP of the invention. While the cannula portion 30 is in an injected state, it can be connected to a fluid collection device CS such those that utilize a blood collection tube or vial or vacutainer type collection tube CV. FIG. 17 shows the fluid collection device CS prior to being connected to the cannula portion 30. FIG. 18 shows the fluid collection device CS connected to the cannula portion 30. FIG. 19 shows the fluid collection device CS connected to the cannula portion 30 and having a blood collection tube CV inserted therein. The devices CS and CV can be of any conventional type provided that they can interface with the cannula portion 30.

Figure 20:
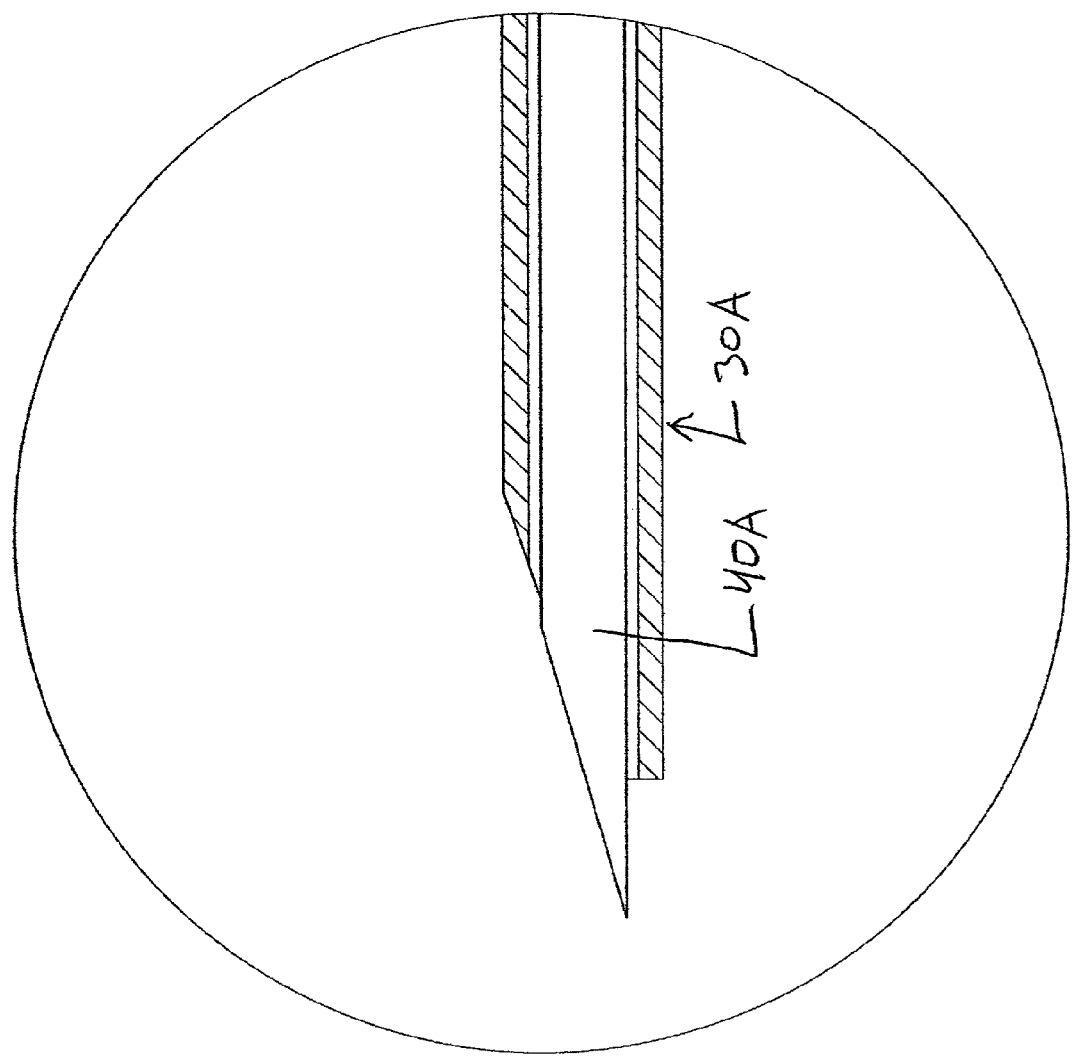
FIG. 20 shows an enlarged view of a puncturing end of the device of FIG. 5.

FIG. 20 shows an enlarged view of a puncturing end of the device shown FIG. 5 and illustrates how the puncturing needle 40A passes through an open end of the cannula 30A. The puncturing needle 40A functions to puncture the skin and, once withdrawn, allows fluid to flow through the cannula 30A.

Figure 21:
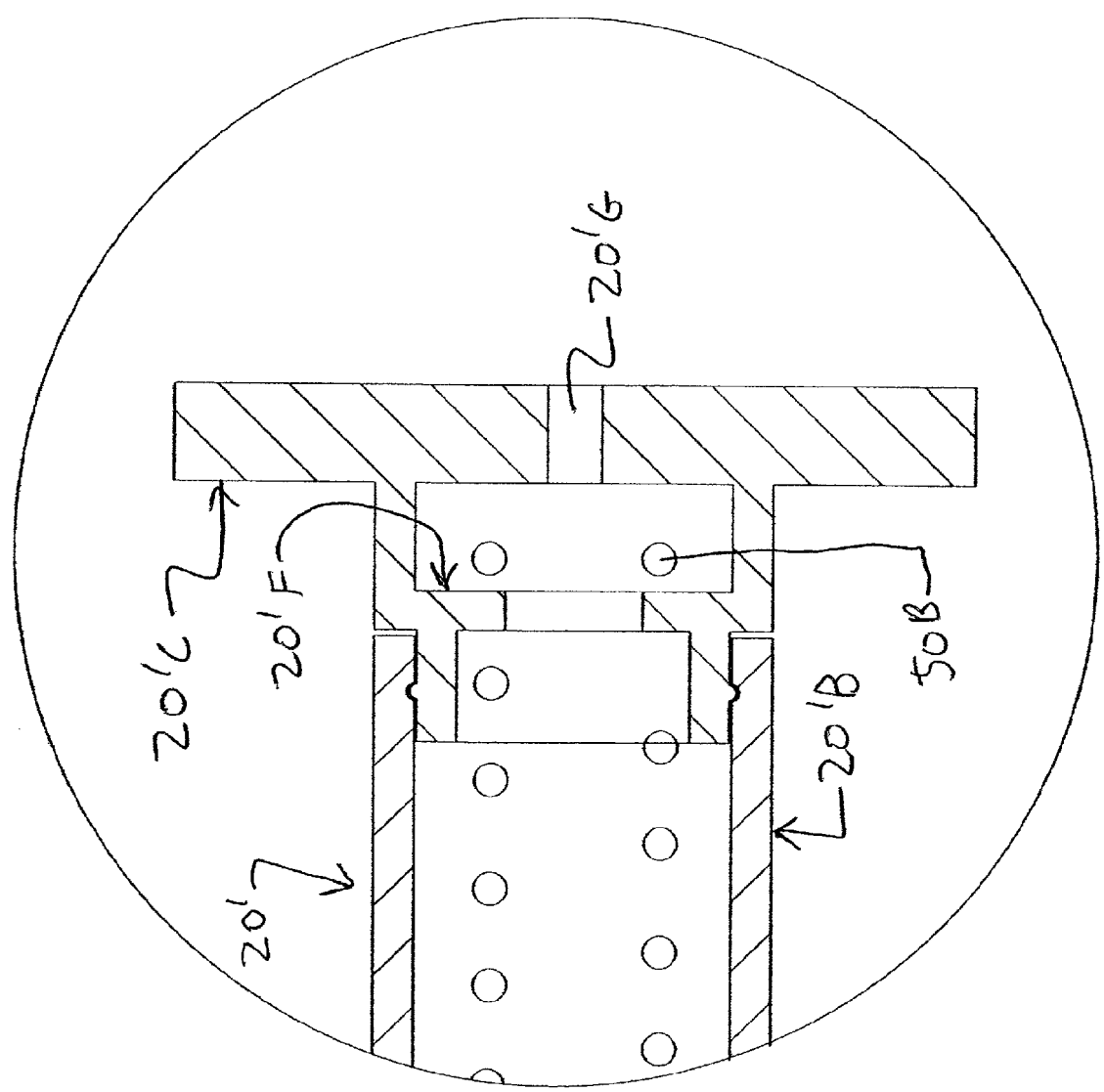
FIG. 21 shows an enlarged view of optional rear end configuration for the device of FIG. 1. In this embodiment, the rear flange portion of the body may be separately formed from a main body portion. This configuration facilitates manufacturing assembly of the device.

FIG. 21 shows an enlarged view of optional rear end configuration for the device of FIG. 1. In this embodiment, the rear flange portion 20'C and the main body 20'B are separately formed and connected together via, e.g., a circumferential engaging recess and projection. This configuration facilitates manufacturing assembly of the device since it allows the needle hub 40 and spring 50 to be inserted into the body from a rear end thereof. Like the embodiment of FIG. 1, a through opening 20'G is disposed at a rear end of the body 20' in order to serve as a vent and to facilitate assembly of the device.

Figure 22A:
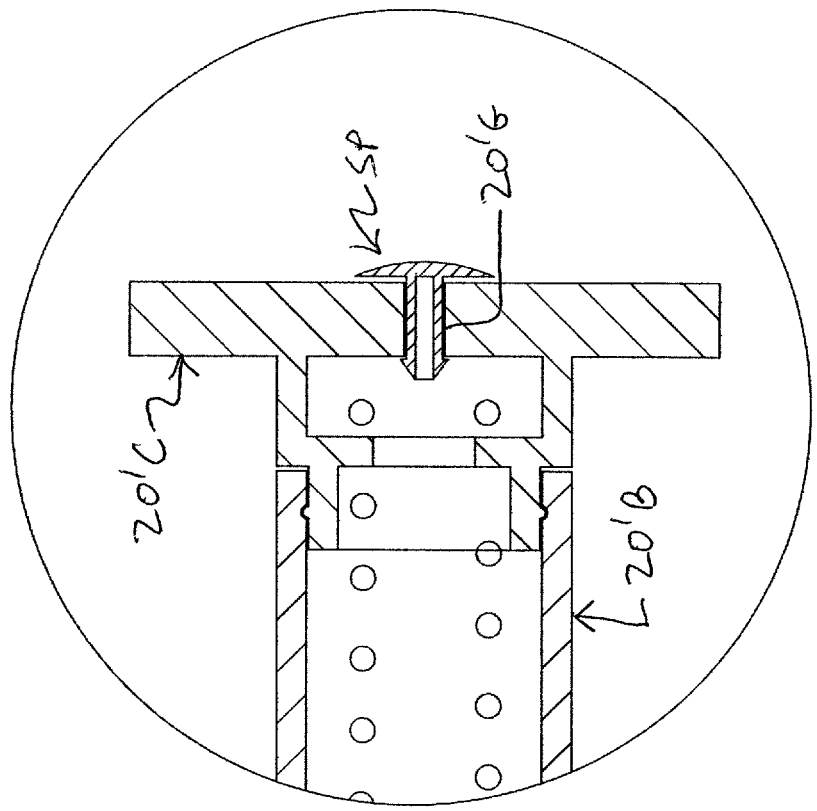
FIG. 22A shows a modified version of FIG. 21 that utilizes a cap to cover a rear opening in the body.
Figure 22B:
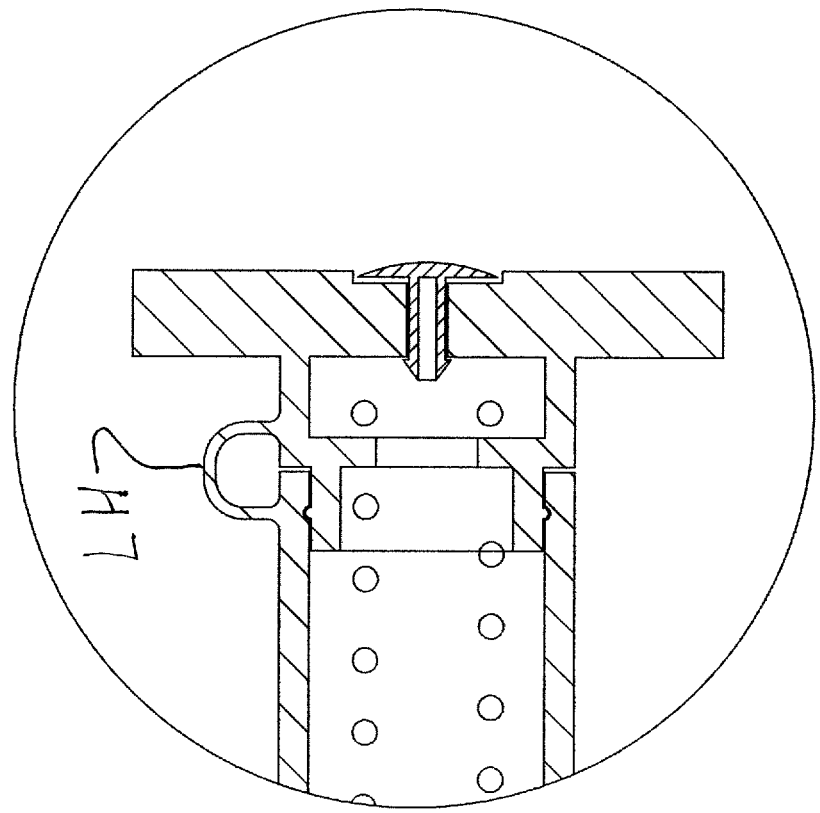
FIG. 22B shows a modified version of FIG. 22A that utilizes a living hinge to connect the rear flange portion to the main body portion which allows both portions to be formed as a one-piece member.

FIG. 22A shows a modified version of FIG. 21 that utilizes a cap SP to cover a rear opening 20'G in the body. FIG. 22B shows a modified version of FIG. 22A that utilizes a living hinge LH to connect the rear flange portion to the main body portion and which allows both portions to be formed as a one-piece member.

Figure 23:
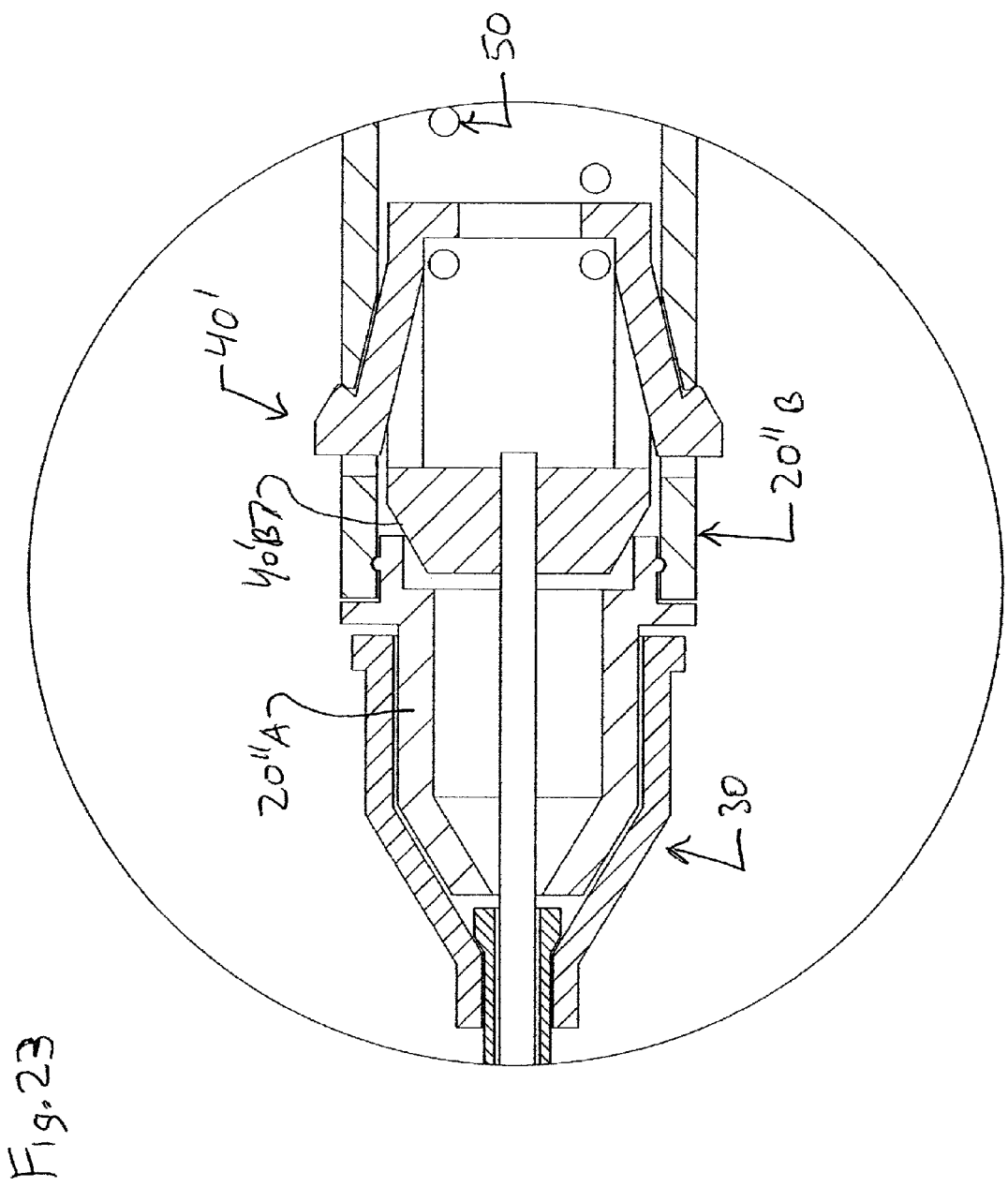
FIG. 23 shows an enlarged view of optional front end configuration for the device of FIG. 1. In this embodiment, the front flange portion of the body is separately formed from a main body portion. This configuration facilitates manufacturing assembly of the device.

FIG. 23 shows an enlarged view of optional front end configuration for the device of FIG. 1. In this embodiment, a front flange portion 20"A is separately formed from a main body portion 20"B. The needle nub 40' is also modified to utilize a front tapered portion 40'B7. This configuration facilitates manufacturing assembly of the device since it allows the needle hub 40' and spring 50 to be inserted into the body from a front end thereof.

Figure 24:
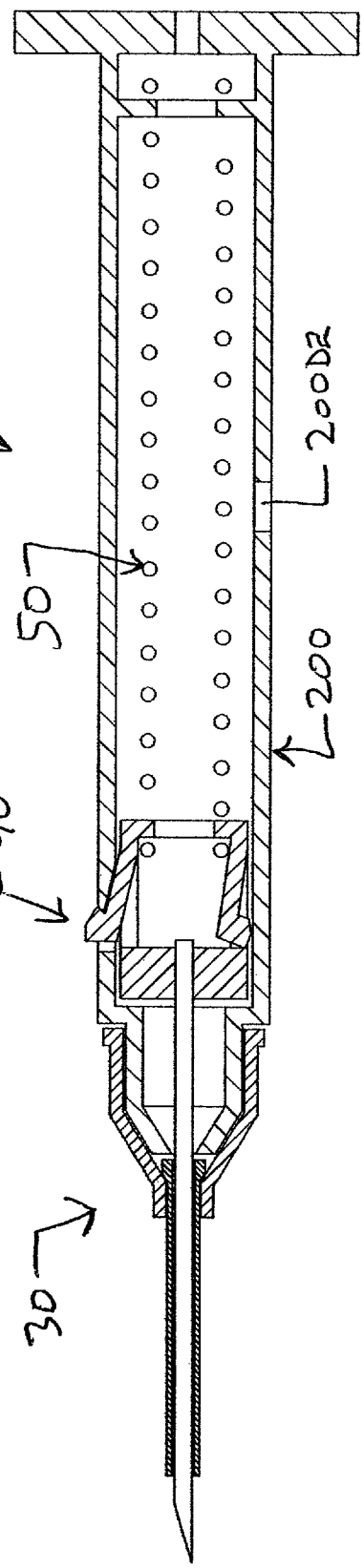
FIG. 24 shows a side cross-section view of another non-limiting embodiment of the device with the protective cap removed. The device is shown in a ready-to-use configuration. This configuration is an injection configuration.
Figure 25:
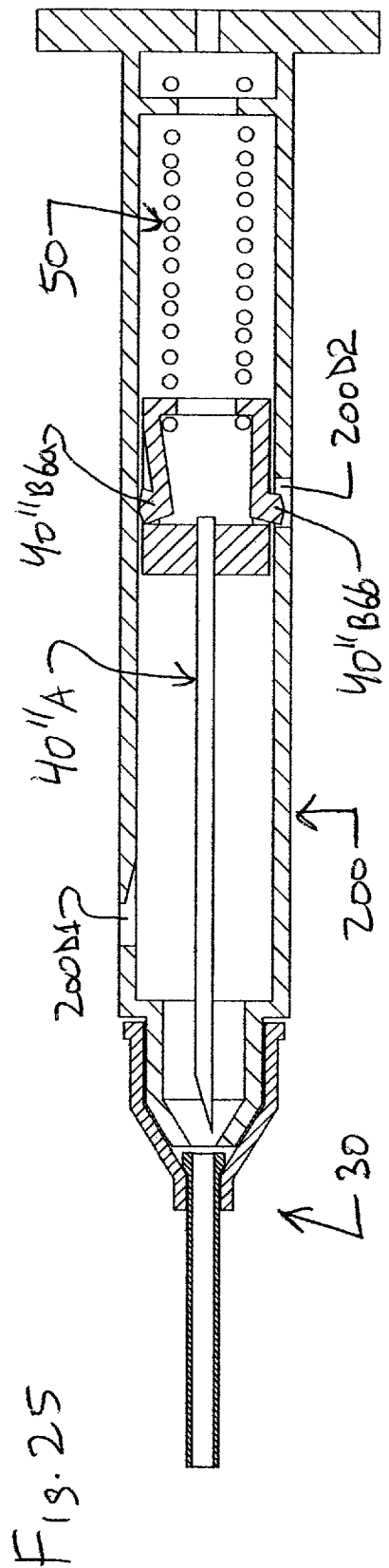
FIG. 25 shows the side cross-section view of FIG. 24 after triggering of the device. As is apparent, the spring which was in tension or axially expanded in FIG. 24 has assumed a relaxed or axially contracted stage thereby withdrawing the puncturing needle into the body of the device.

FIGS. 24 and 25 show another non-limiting embodiment of the device, which like that of FIG. 5, utilizes a cannula portion 30 and a tool portion TP'. In FIG. 24, the device is shown in a ready-to-use configuration. This is the configuration which allows a user of the device to inject it into the skin. FIG. 25 shows the device of FIG. 24 after triggering. As is apparent, the spring 50 which was in tension or axially expanded in FIG. 24 has assumed a relaxed or axially contracted state thereby withdrawing the puncturing needle 40" into the body 200 of the device. In this embodiment, only one deflectable retaining member 40"B6a is used to retain, via opening 200D1, the needle hub 40" in the trigger-set position shown in FIG. 24. Once triggered, another deflectable retaining member 40"B6b is used to retain, via opening 200D2, the needle hub 40" in the retracted position shown in FIG. 25. In embodiments, the features of FIGS. 1 and 24 can be combined so that two openings of the type, e.g., 20D1, shown in FIG. 1 and utilized as well as two openings of the type, e.g., 200D2, are used with the latter openings being offset by 90 degrees. In this embodiment, the needle hub 40/40" would utilize four deflectable retaining members (not shown).

Figure 26:
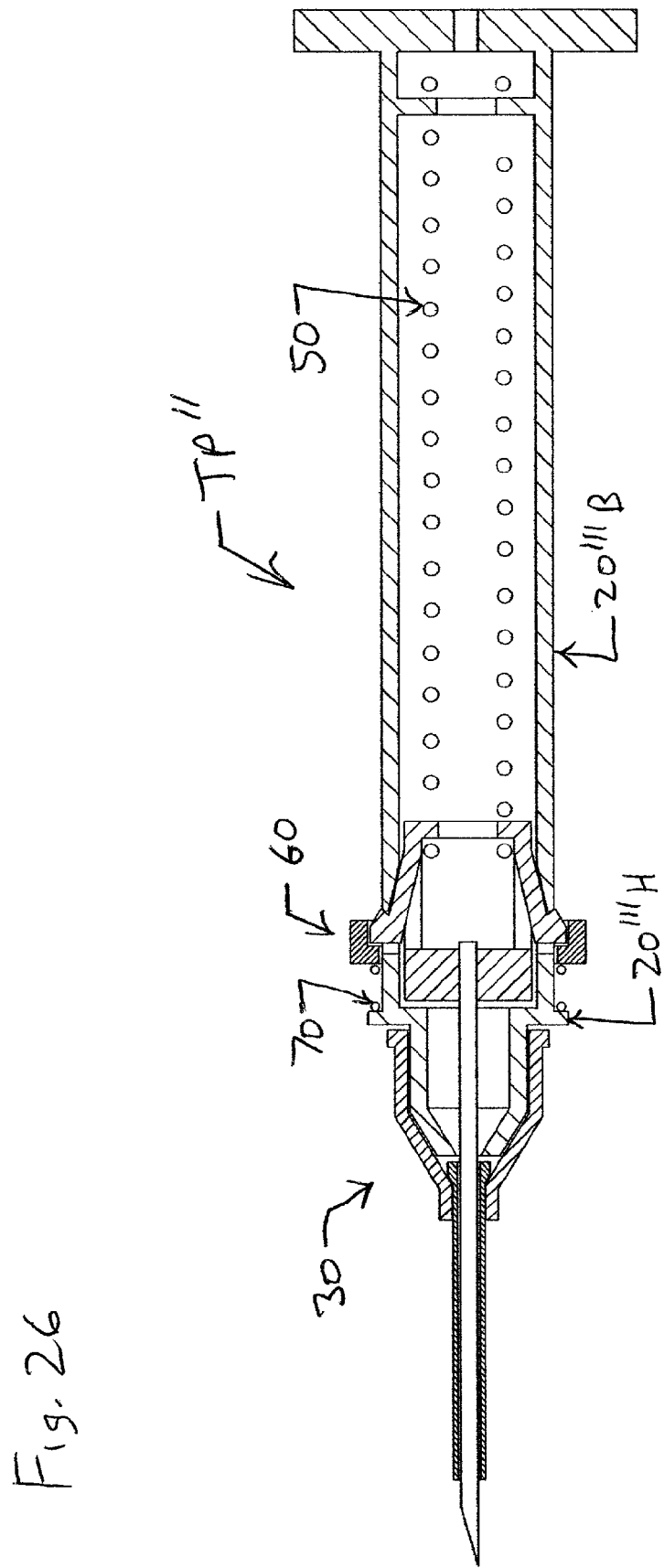
FIG. 26 shows a side cross-section view of still another non-limiting embodiment of the device with the protective cap removed. The device is shown in a ready-to-use configuration. This configuration is an injection configuration.
Figure 27:
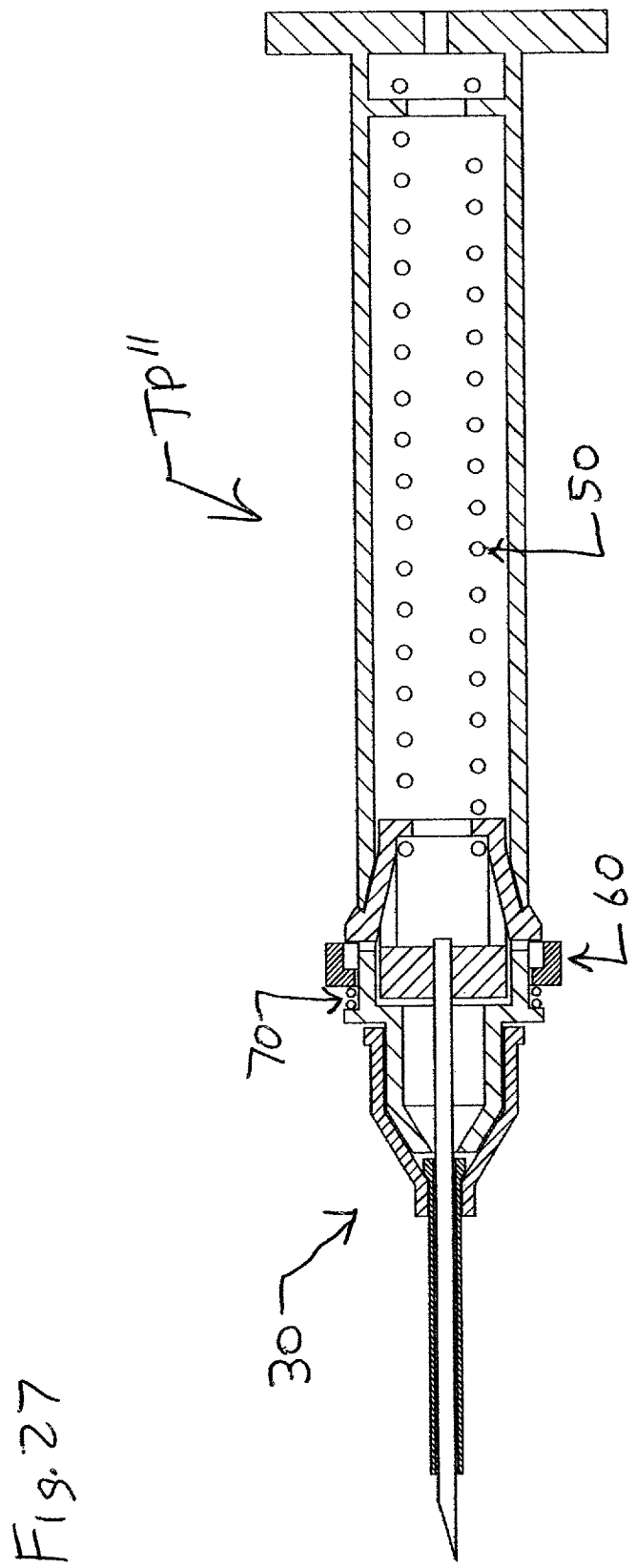
FIG. 27 shows the side cross-section view of FIG. 26 during release of a safety prior to triggering of the device. With the safety retracted, the device can be triggered in the same manner as was shown in FIG. 7.

FIGS. 26 and 27 show another non-limiting embodiment of the device, which like that of FIG. 5, utilizes a cannula portion 30 and a tool portion TP'''. In FIG. 26, the device is shown in a ready-to-use or trigger-set configuration. This is the configuration which allows a user of the device to inject the cannula portion 30 into the skin and/or tissue. FIG. 27 shows the device of FIG. 26 after a trigger safety 60 is retracted against the biasing force of the a spring 70 so as to ready the device for triggering. To trigger the device, the user can use his or her thumb and forefinger to first retract the ring 70 and then cause triggering of the device in the same way as shown in FIG. 7.

Figure 28:
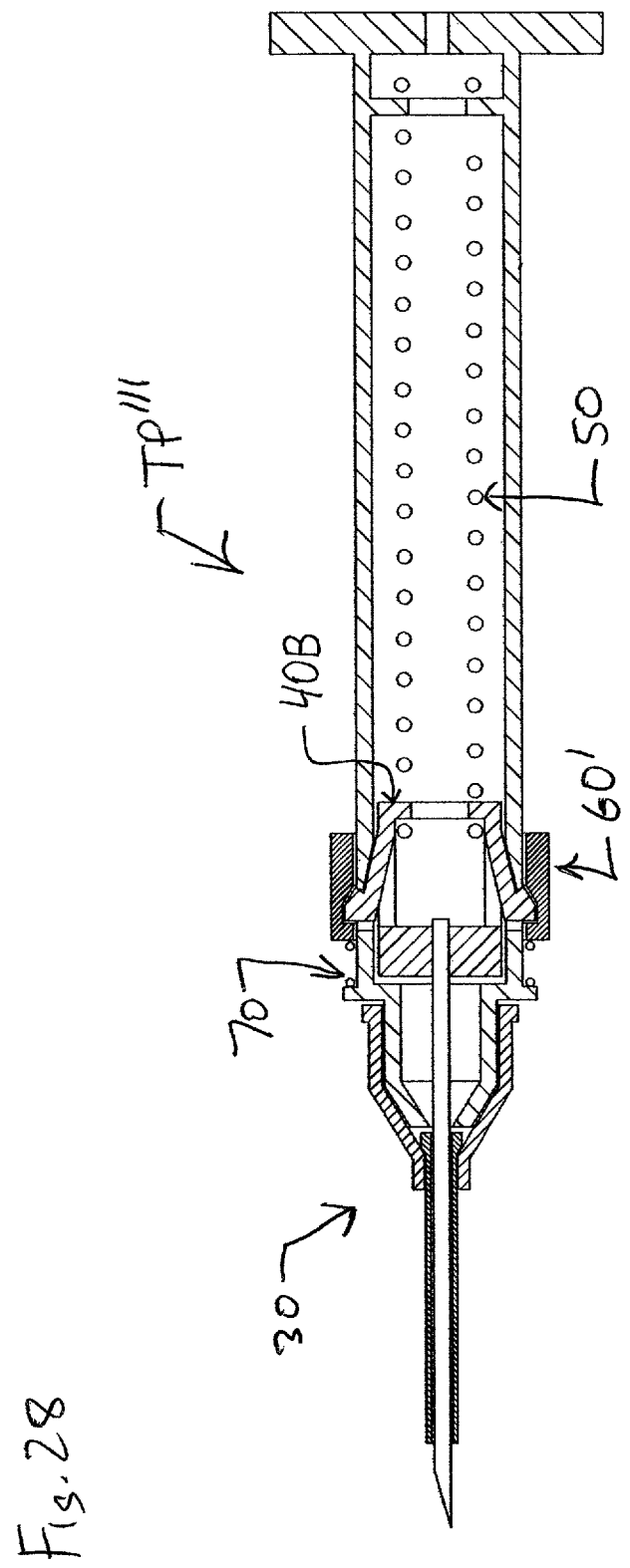
FIG. 28 shows a side cross-section view of still another non-limiting embodiment of the device with the protective cap removed. The device is shown in a ready-to-use configuration. This configuration is an injection configuration. In this embodiment, the device is triggered by axial movement of a trigger ring against the biasing force of a trigger spring.

FIG. 28 shows another non-limiting embodiment of the device, which like that of FIG. 5, utilizes a cannula portion 30 and a tool portion TP'''. In FIG. 28, the device is shown in a ready-to-use or trigger-set configuration. This is the configuration which allows a user of the device to inject the cannula portion 30 into the skin and/or tissue. This embodiment allows a user to use axial movement of a trigger ring 60' to cause triggering of the device. Thus, triggering occurs when the trigger ring 60' is moved against the biasing force of the a spring 70 to the point where the ring 60' causes the deflectable retaining members of the needle hub 40B to disengage from the openings of the body. To trigger the device, the user can use his or her thumb and forefinger to move the ring 60 forwards until the deflectable retaining members to disengage from the openings of the body.

Figure 29:
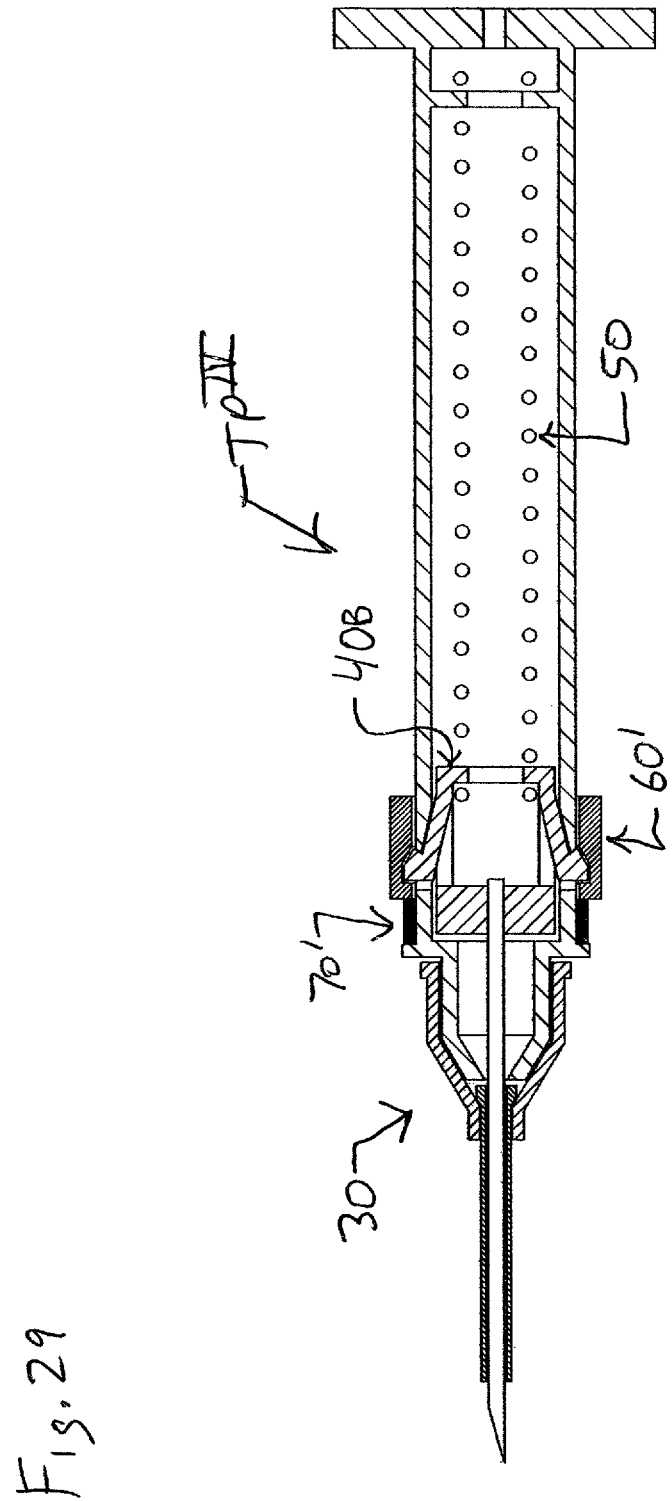
FIG. 29 shows a side cross-section view of still another non-limiting embodiment of the device with the protective cap removed. The device is shown in a ready-to-use configuration. This configuration is an injection configuration. In this embodiment, the device is triggered by axial movement of the trigger ring against the biasing force of a biasing ring.

FIG. 29 shows another non-limiting embodiment of the device, which like that of FIG. 5, utilizes a cannula portion 30 and a tool portion TP$^{IV}$. In FIG. 29, the device is shown in a ready-to-use or trigger-set configuration. This is the configuration which allows a user of the device to inject the cannula portion 30 into the skin and/or tissue. This embodiment allows a user to use axial movement of a trigger ring 60' to cause triggering of the device. Thus, triggering occurs when the trigger ring 60' is moved against the biasing force of the an elastic ring 70' to the point where the ring 60' causes the deflectable retaining members of the needle hub 40B to disengage from the openings of the body. To trigger the device, the user can use his or her thumb and forefinger to move the ring 60' forwards until the deflectable retaining members to disengage from the openings of the body.

Figure 30:
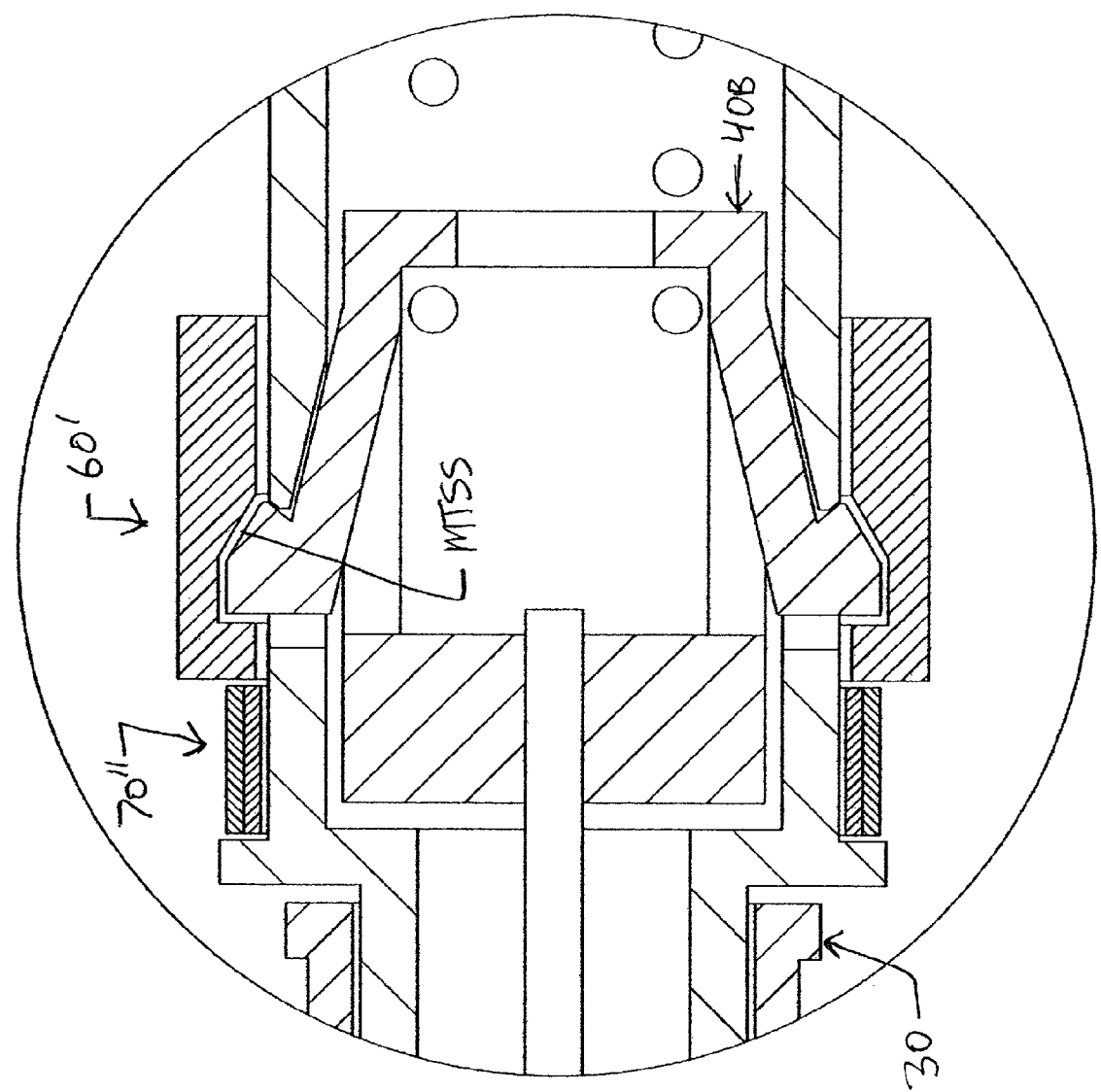
FIG. 30 shows an enlarged partial side cross-section view of still another non-limiting embodiment of the device with the protective cap removed. The device is shown in an almost ready-to-use configuration. Once the user removes a safety tape/ring that will allows for axial movement of the trigger ring, the device can be injected into the skin. In this embodiment, the device may also be triggered by axial movement of the trigger ring.

FIG. 30 shows another non-limiting embodiment of the device, which like that of FIG. 5, utilizes a cannula portion 30 and a tool portion. In FIG. 30, the device is shown in a ready-to-use or trigger-set configuration. This is the configuration which allows a user of the device to inject the cannula portion into the skin and/or tissue. This embodiment allows a user to use axial movement of a trigger ring 60' to cause triggering of the device. First, however, the user must remove a removable trigger safety tape or safety ring 70" which prevents forward movement of the trigger ring 60'. Thus, triggering occurs when the user removes the safety tape 70" and then moves trigger ring 60' to the point where the ring 60' causes the deflectable retaining members of the needle hub 40B to disengage from the openings of the body. To trigger the device, the user can use his or her thumb and forefinger to move the ring 60' forwards until the deflectable retaining members to disengage from the openings of the body. In a manner similar to the embodiments of FIGS. 28 and 29, the trigger ring 60' has an internal tapered surface which engages with the movable tapered sliding surface MTSS of each deflectable retaining member of the need hub 40B.

Figure 31:
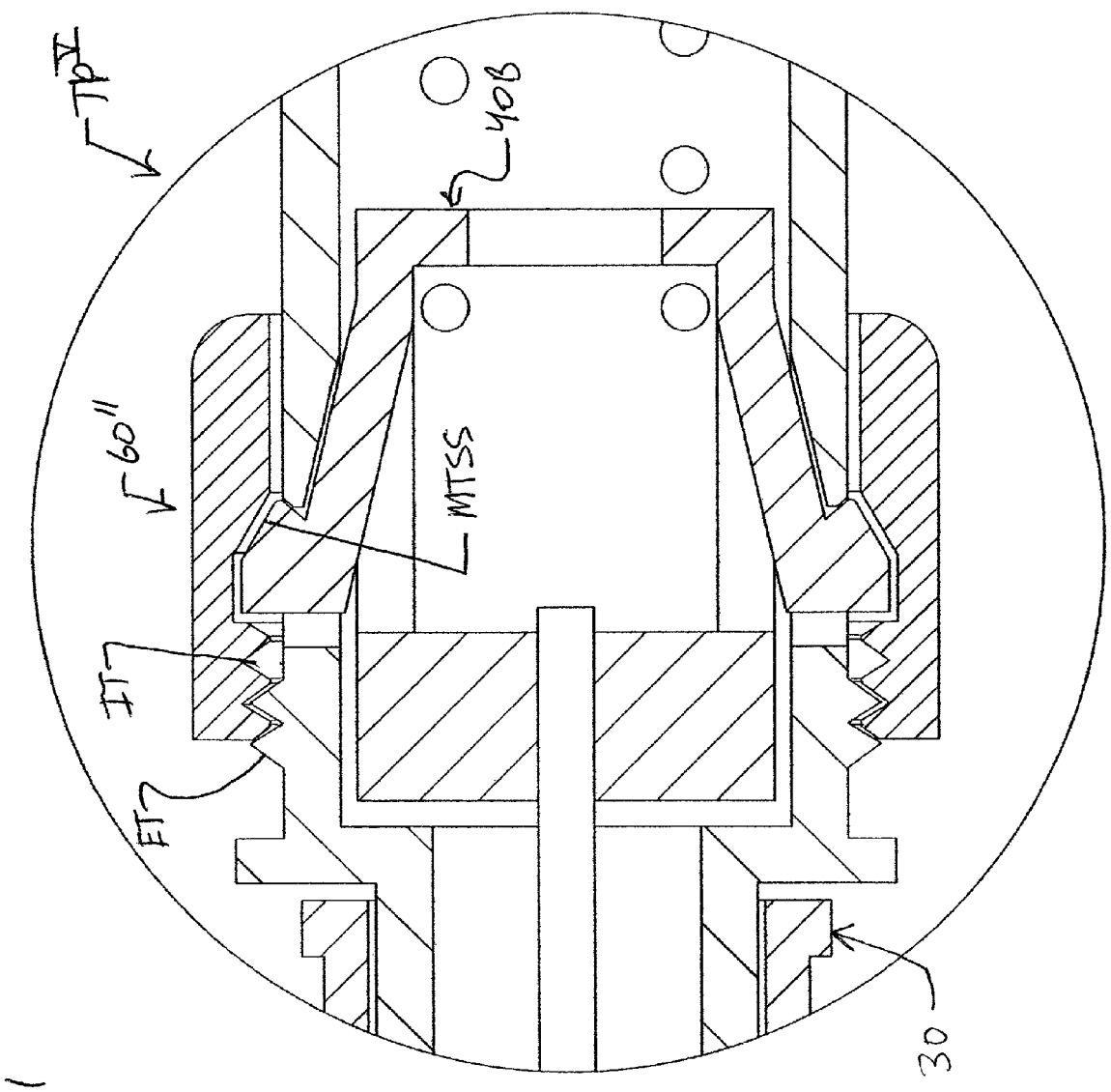
FIG. 31 shows an enlarged partial side cross-section view of still another non-limiting embodiment of the device with the protective cap removed. The device is shown in a ready-to-use configuration. This configuration is an injection configuration. In this embodiment, the device is triggered by rotating the trigger ring so that engagement between its internal threads and the external threads of the body cause axial movement of the trigger ring to the point where the device is triggered.

FIG. 31 shows another non-limiting embodiment of the device, which like that of FIG. 5, utilizes a cannula portion 30 and a tool portion TP$^V$. In FIG. 31, the device is shown in a ready-to-use or trigger-set configuration. This is the configuration which allows a user of the device to inject the cannula portion into the skin and/or tissue. This embodiment allows a user to use axial and rotating (i.e., threading) movement of a trigger ring 60" to cause triggering of the device. The threaded engagement between internal threads IT of the ring 60" and external threads ET of the body form a safety which prevents mere axial movement of the ring 60" from triggering the device. Thus, triggering occurs when the user threadably rotates the trigger ring 60" to the point where the ring 60" causes the deflectable retaining members of the needle hub 40B to disengage from the openings of the body. To trigger the device, the user can use his or her thumb and forefinger to rotate the ring 60" so that it moves axially forwards until the deflectable retaining members to disengage from the openings of the body. In a manner similar to the embodiments of FIGS. 28-30, the trigger ring 60" has an internal tapered surface which engages with the movable tapered sliding surface MTSS of each deflectable retaining member of the need hub 40B.

Figure 32:
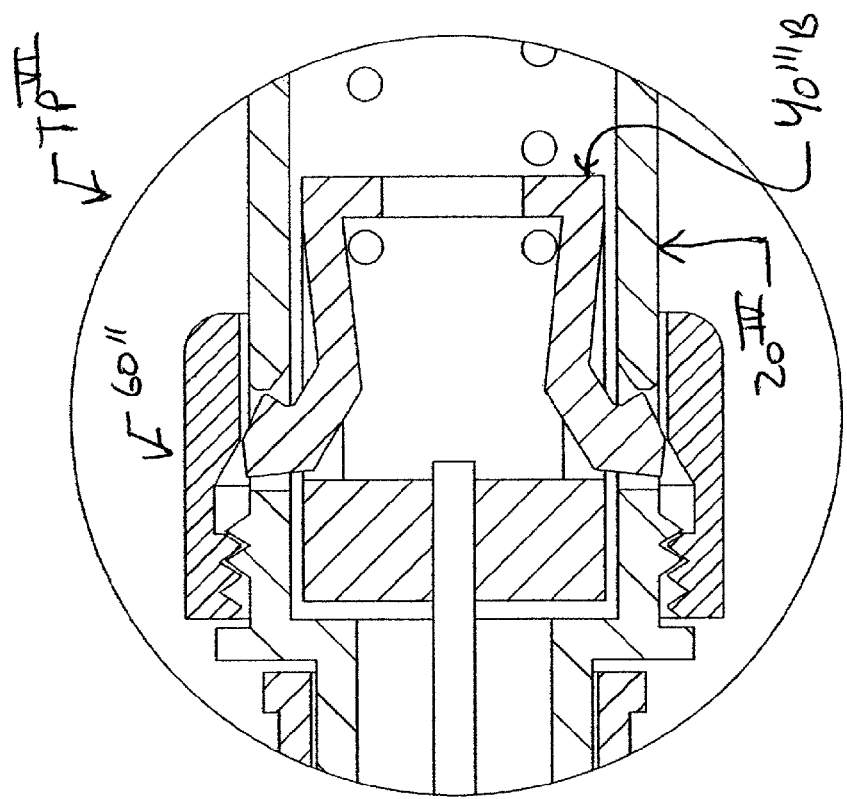
FIGS. 32 and 33 show a modified version of the device of FIG. 31.
Figure 33:
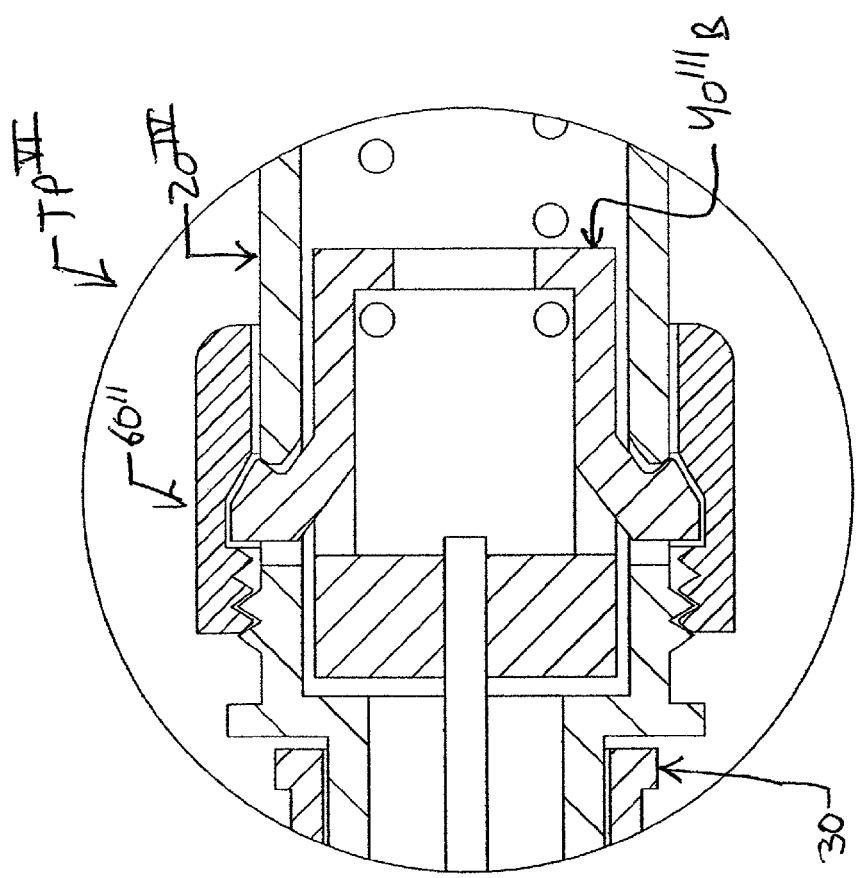

FIGS. 32 and 33 show another non-limiting embodiment of the device, which like that of FIG. 5, utilizes a cannula portion 30 and a tool portion TP$^{VI}$. In FIG. 32, the device is shown in a ready-to-use or trigger-set configuration. This is the configuration which allows a user of the device to inject the cannula portion into the skin and/or tissue. This embodiment is different from that of FIG. 31 in that the need hub 40'''B utilizes different configured deflecting arms connecting the deflectable retaining members to the needle hub 40'''B. This embodiment similarly allows a user to use axial and rotating (i.e., threading) movement of a trigger ring 60" to cause triggering of the device as shown in FIG. 33. The threaded engagement between internal threads of the ring 60" and external threads of the body 20$^{IV}$ form a safety which prevents mere axial movement of the ring 60" from triggering the device. Thus, triggering occurs when the user threadably rotates the trigger ring 60" (from the position shown in FIG. 32) to the point where the ring 60" causes (in the position shown in FIG. 33) the deflectable retaining members of the needle hub 40B to disengage from the openings of the body 20$^{IV}$. To trigger the device, the user can use his or her thumb and forefinger to rotate the ring 60" so that it moves axially forwards until the deflectable retaining members to disengage from the openings of the body 20$^{IV}$. In a manner similar to the embodiments of FIGS. 28-31, the trigger ring 60" has an internal tapered surface which engages with the movable tapered sliding surface of each deflectable retaining member of the need hub $40'''$B.

FIGS. 34 and 34a show still another non-limiting embodiment of the device, which like that of FIG. 5, utilizes a cannula portion 30 and a tool portion TP$^{VII}$. In FIG. 34, the device is shown in a ready-to-use or trigger-set configuration. This is the configuration which allows a user of the device to inject the cannula portion into the skin and/or tissue. The device utilizes a trigger including a first part 80a and a second part 80b. A spring TRS biases the first part 80a towards the second part 80b A circumferential projection engages with a tapered surface of the member 80b (as shown in FIG. 34a). In this embodiment, the device is triggered by axial forward movement of, i.e., by depressing, a rearward extending trigger button of the member 80b which causes the end of the member 80a having the projection (see FIG. 34a) to pass into the hollow space of the member 80b. Once the engagement shown in FIG. 34a fails, the spring 50 causes the needle member $40^{IV}$B to retract into the body $20^{V}$.

FIGS. 35 and 35a show still another non-limiting embodiment of the device, which like that of FIG. 5, utilizes a cannula portion 30 and a tool portion TP$^{VIII}$. In FIG. 35, the device is shown in a ready-to-use or trigger-set configuration. This is the configuration which allows a user of the device to inject the cannula portion into the skin and/or tissue. The device utilizes a trigger including a first part 80'a and a second part 80'b. A breakable section BS (see FIG. 35a) connects these sections. A spring TRS biases the first and second parts towards the read side of the device. In this embodiment, the device is triggered by axial forward movement of, i.e., by depressing, a rearward extending trigger button of the member 80'b which causes the end of the forward end of the member 80'a to move forwards and compress the spring TRS. This, in turn, allows the deflectable retaining members of the needle hub $40^{IV}$B to deflect inwardly a slight amount and disengage from the openings of the body $20^{V}$. As the needle nub $40^{IV}$B is retracted by the spring 50, the members 80'a and 80'b are caused to move rearwards until the area of the breakable section BS reaches the opening $20^{V}$G. As this point, the user cab deflect the 80'b until the section BS breaks and discard the same.

FIGS. 36-38 show another non-limiting embodiment of the device, which like that of FIG. 5, utilizes a cannula portion 30 and a tool portion TP$^{IX}$. In FIG. 36, the device is shown in a ready-to-use or trigger-set configuration. This is the configuration which allows a user of the device to inject the cannula portion 30 into the skin and/or tissue. This embodiment allows a user to use axial movement of a trigger sleeve 60''' to cause triggering of the device. Thus, triggering occurs when the trigger ring 60''' is moved back against the biasing force of the a spring 70 to the point where the ring 60''' causes the deflectable retaining members of the needle hub $40^{V}$B to disengage from the openings of the body $20^{VI}$. To trigger the device, the user can use his or her thumb and place it on the rear surface of the flange of the body $20^{VI}$ and then place the forefinger and middle finger in front of the flange 60'''d of the trigger sleeve 60'''. The user can then use a squeezing motion (similar to that used with an injection syringe) to move the ring 60''' rearwards until the deflectable retaining members of the hub $40^{V}$B to disengage from the openings of the body $20^{VI}$. FIGS. 37 and 38 show the trigger sleeve 60''' used in the device of FIG. 36. The trigger sleeve 60''' includes a tapered surface 60'''a configured to engage with a tapered surface of the deflectable retaining members of the hub $40^{V}$B, a circumferential groove receive therein the deflectable retaining members of the hub $40^{V}$B, a generally cylindrical portion 60'''c, a flange 60'''d, and a rear recess 60'''e.

Figure 39:
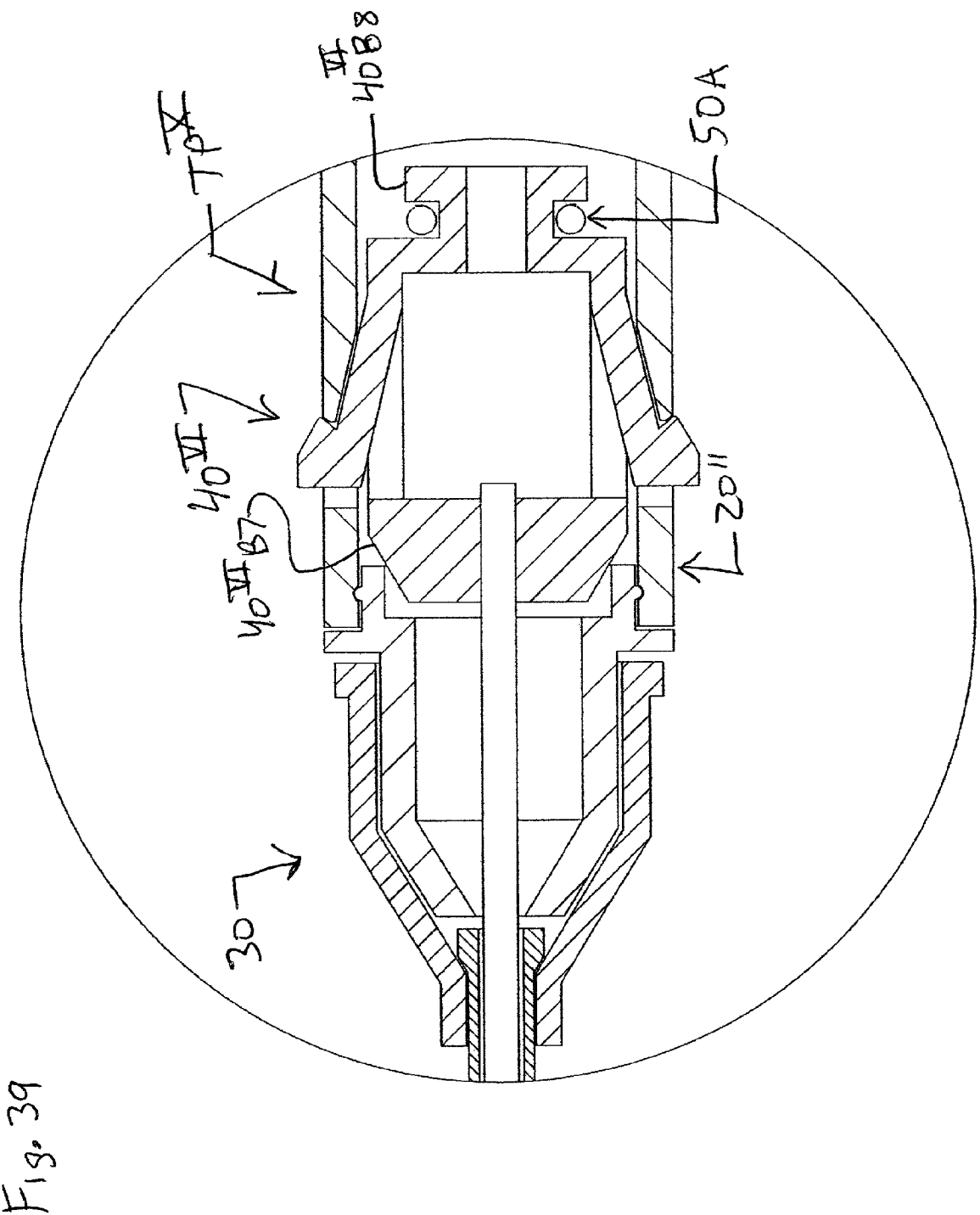
FIG. 39 shows an enlarged view of optional front end configuration for any of the devices shown above such as that shown in FIG. 1. In this embodiment, the front flange portion of the body is separately formed from a main body portion. The puncturing needle hub also has modified configuration. This configuration facilitates manufacturing assembly of the device.

FIG. 39 shows an enlarged view of optional front end configuration for the device of FIG. 23. In this embodiment, the device has a tool portion TP$^{X}$ that utilizes a needle nub $40^{VI}$ having a front tapered portion $40^{VI}$B7 and a rear projection $40^{VI}$B8 for connecting to a front end 50A of the spring 50. This configuration facilitates manufacturing assembly of the device since it allows the needle hub 40' and spring 50 to be inserted into the body 20'' from a front end thereof.

Figure 40:
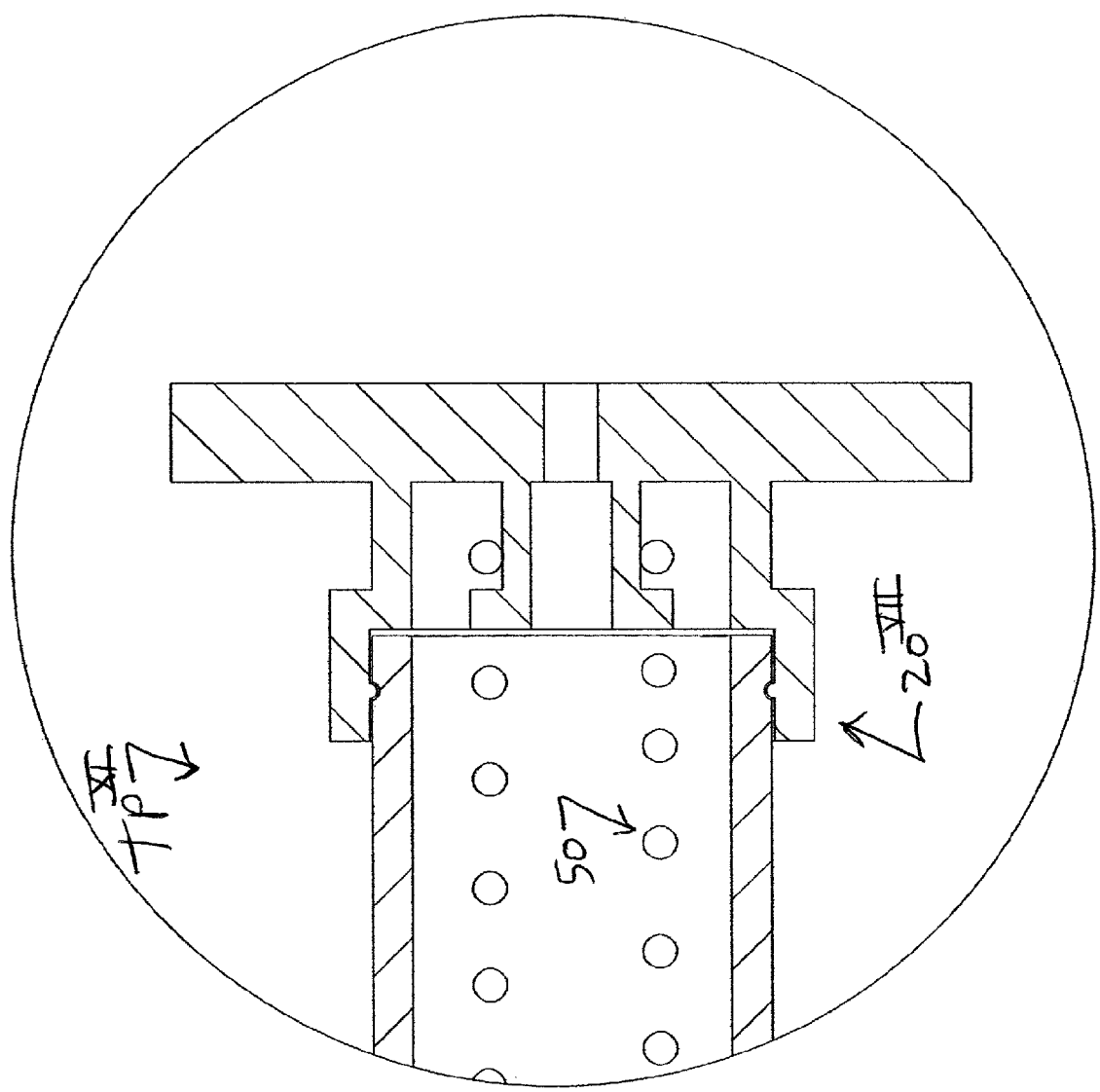
FIG. 40 shows an enlarged view of optional rear end configuration for the device of FIG. 1. In this embodiment, the rear flange portion of the body is separately formed from a main body portion. This configuration facilitates manufacturing assembly of the device.

FIG. 40 shows an enlarged view of optional rear end configuration for the device of FIG. 1. In this embodiment, the rear flange portion and the body $20^{VII}$ are separately formed and connected together via, e.g., a circumferential engaging recess and projection. This configuration facilitates manufacturing assembly of the device since it allows the needle hub and spring 50 to be inserted into the body from a rear end thereof. Like the embodiment of FIG. 1, a through opening is disposed at a rear end of the body $20^{VII}$ in order to serve as a vent and to facilitate assembly of the device.

Figure 41:
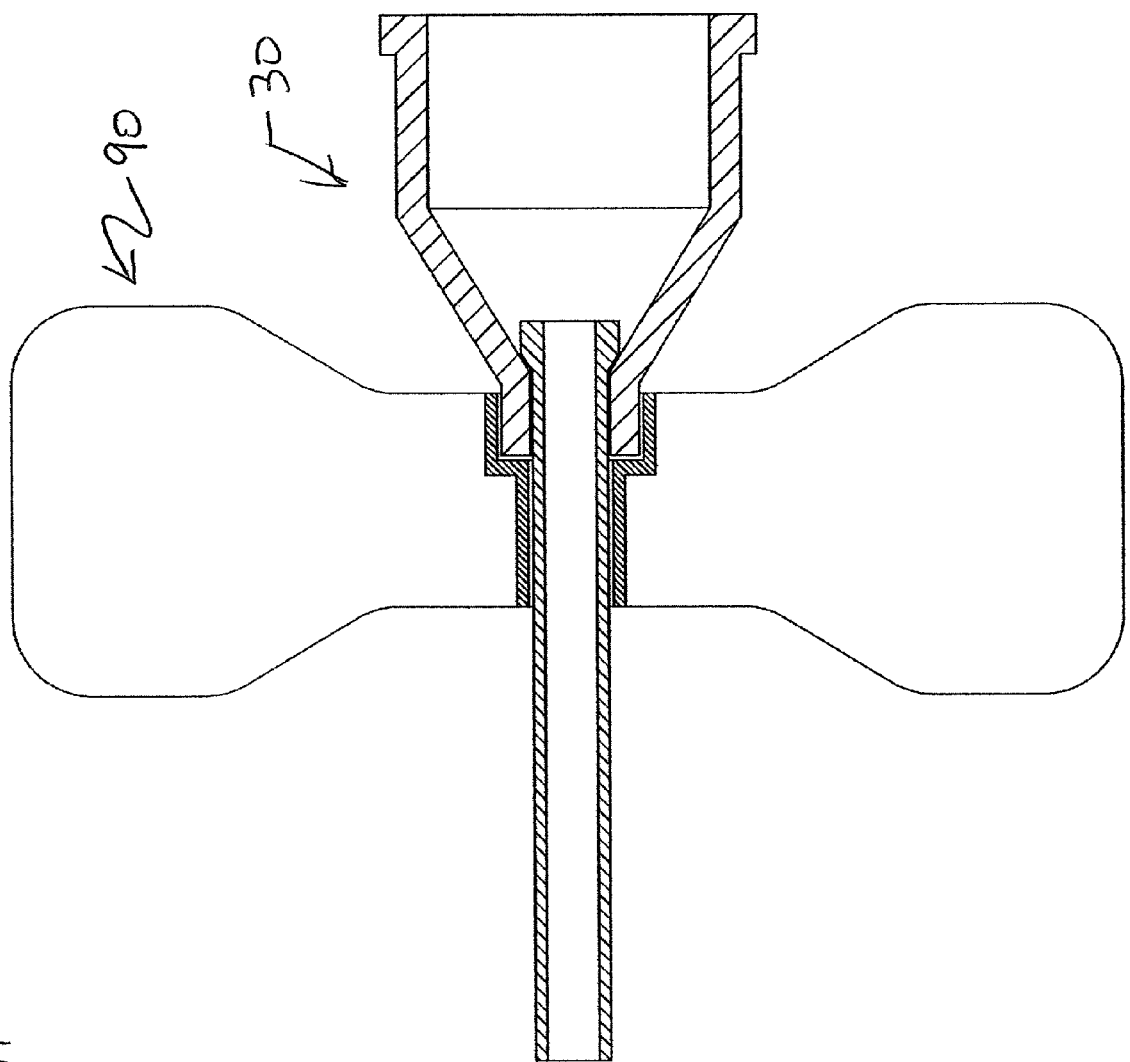
FIG. 41 shows a side cross-section view of a cannula assembly that can be used on any of the devices shown above such as that shown in FIG. 1. In this embodiment, the cannula utilizes a butterfly type member.
Figure 43:
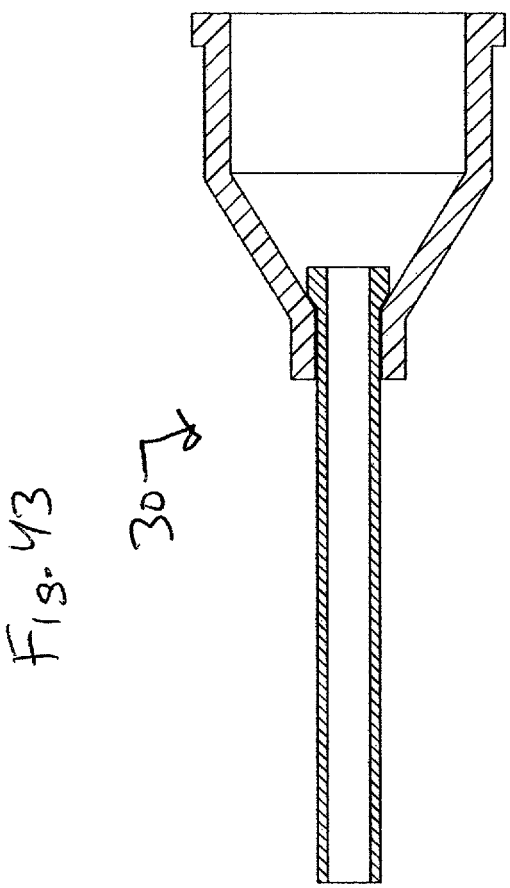
FIG. 43 shows the side cross-section view of the cannula portion shown in FIG. 41.
Figure 42:
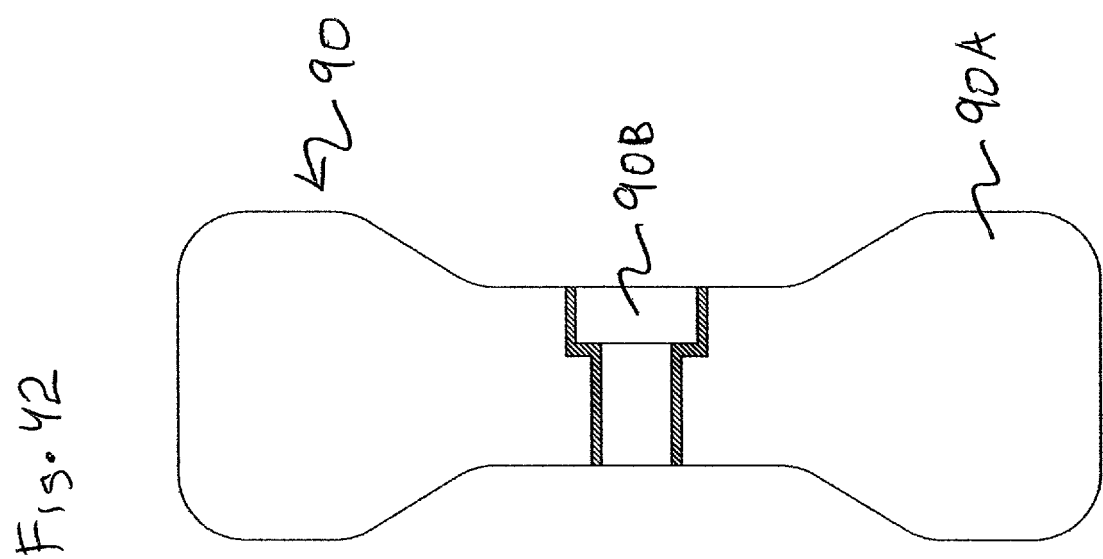
FIG. 42 shows the side cross-section view of the butterfly member shown in FIG. 41.

FIGS. 41-43 show a cannula assembly that can be used on any of the devices shown herein such as that shown in FIG. 1. In this embodiment, the cannula 30 utilizes a butterfly type member 90 to allow the cannula to be more securely retained on a user's skin. Butterfly type devices are well known and are therefore not described herein in detail.

FIGS. 44 and 45 show another embodiment of the device according to the invention. The device is shown after triggering of the device. The device is similar to that of FIG. 1. However, unlike the device shown in FIG. 1, this device uses a known luer lock type connection between the cannula portion 300 and the tool portion TP$^{XII}$. As is apparent, the spring which was, prior to triggering, in tension or axially expanded has assumed a relaxed or axially contracted state thereby withdrawing the puncturing needle into the body $20^{VIII}$ of the device.

FIGS. 46 and 47 show another embodiment of the device according to the invention. The device is shown after triggering of the device. Unlike the device shown in FIGS. 45 and 46, this device can be used after it is utilized to install a cannula portion shown in FIGS. 44 and 45. FIG. 46 shows that the tool portion TP$^{XII}$ can be used again by connecting it to a different cannula portion 100. Since the puncturing needle remains safely disposed in the body of the tool portion TP$^{XII}$, there is no danger of pricking by re-using the device TP$^{XII}$.

Figure 48:
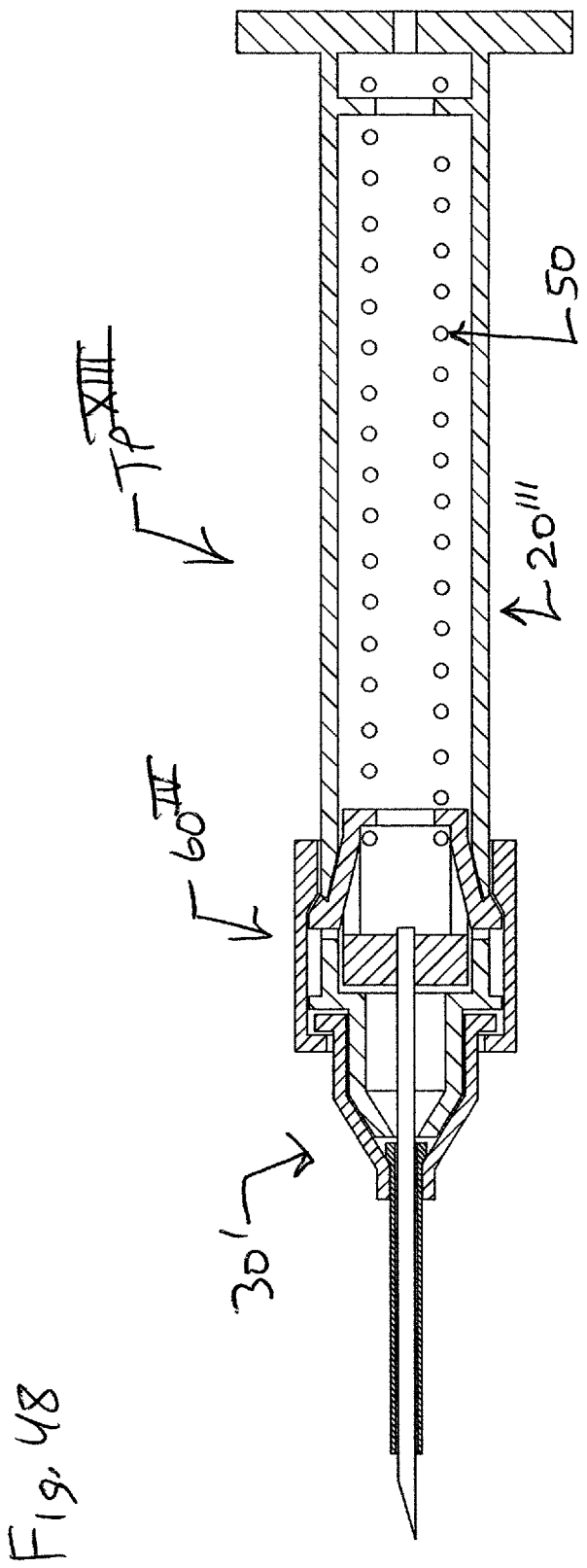
FIG. 48 shows a side cross-section view of still another non-limiting embodiment of the device with the protective cap removed. The device is shown in a ready-to-use configuration. This configuration is an injection configuration. In this embodiment, the device is triggered by axial movement of a trigger sleeve. The device and/or trigger sleeve is then rotated to allow the device to be disconnected from the cannula portion.
Figure 49:
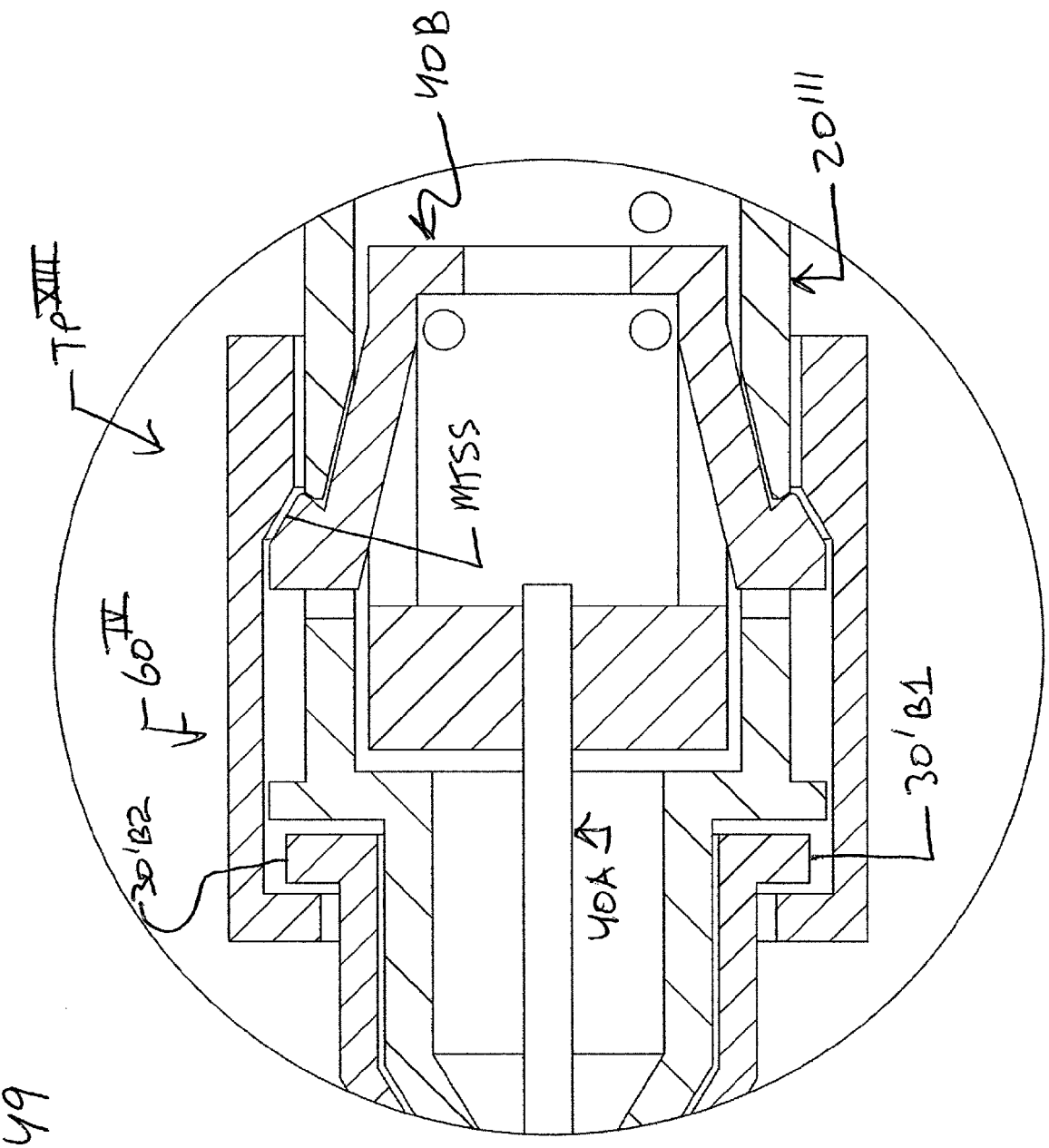
FIG. 49 shows an enlarged view of a triggering/retaining portion of the device of FIG. 48.
Figure 51:
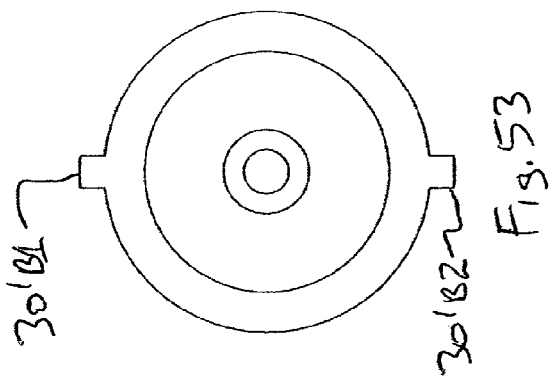
FIG. 51 shows a side cross-section view of the trigger sleeve used in the device of FIG. 48.
Figure 50:
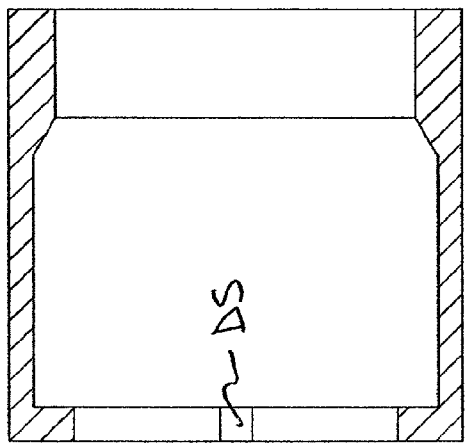
FIG. 50 shows a front end view of the trigger sleeve used on the device of FIG. 48.
Figure 52:
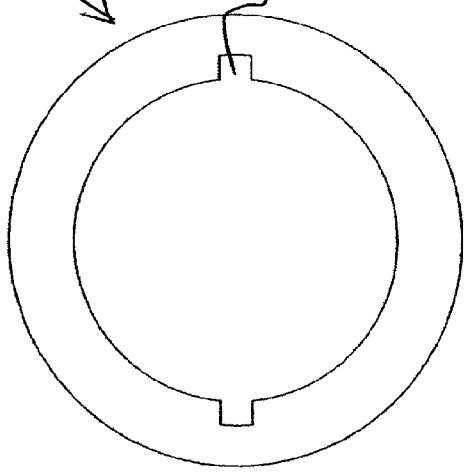
FIG. 52 shows a side cross-section view of the cannula portion used in the device of FIG. 48.
Figure 53:
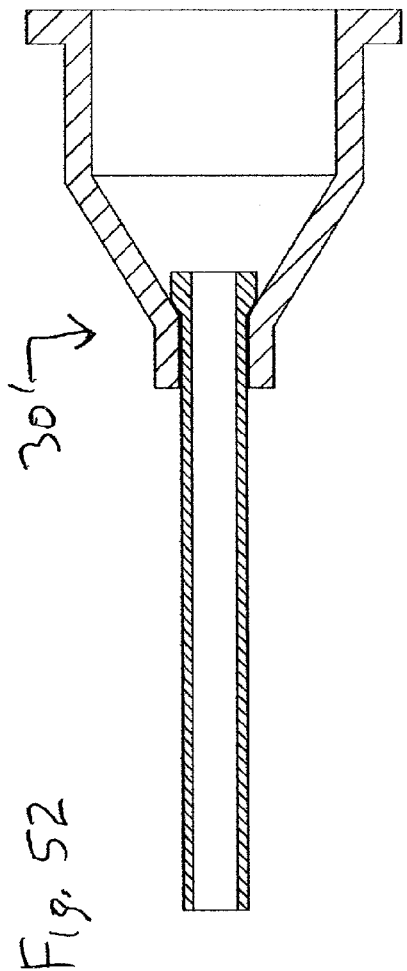
FIG. 53 shows a rear end view of the cannula portion used on the device of FIG. 48.

FIGS. 48-53 show another non-limiting embodiment of the device, which like that of FIG. 5, utilizes a cannula portion 30' and a tool portion TP$^{XIII}$. In FIG. 48, the device is shown in a ready-to-use or trigger-set configuration. This is the configuration which allows a user of the device to inject the cannula portion 30' into the skin and/or tissue. This embodiment allows a user to use axial movement of a trigger sleeve $60^{IV}$ to cause triggering of the device. Thus, triggering occurs when the trigger ring $60^{IV}$ is moved forwards to the point where the sleeve $60^{IV}$ causes the deflectable retaining members of the needle hub 40B to disengage from the openings of the body 20'''. To trigger the device, the user can use his or her thumb and forefinger to move the ring $60^{IV}$ forwards until the tapered surfaces MTSS are contacted and moved by the corresponding surfaces of the trigger sleeve $60^{IV}$ to the point where the deflectable retaining members to disengage from the openings of the body. After triggering, the user can disconnect the cannula portion 30' and the tool portion TP$^{XIII}$ by either rotating the sleeve $60^{IV}$ and/or rotating the tool portion TP$^{XIII}$ to the point wherein the projections 30'B1 and 30'B2 align with the recesses DS. Then, the user can withdraw the tool portion TP$^{XIII}$ axially away from the cannula portion 30'.

Figure 54:
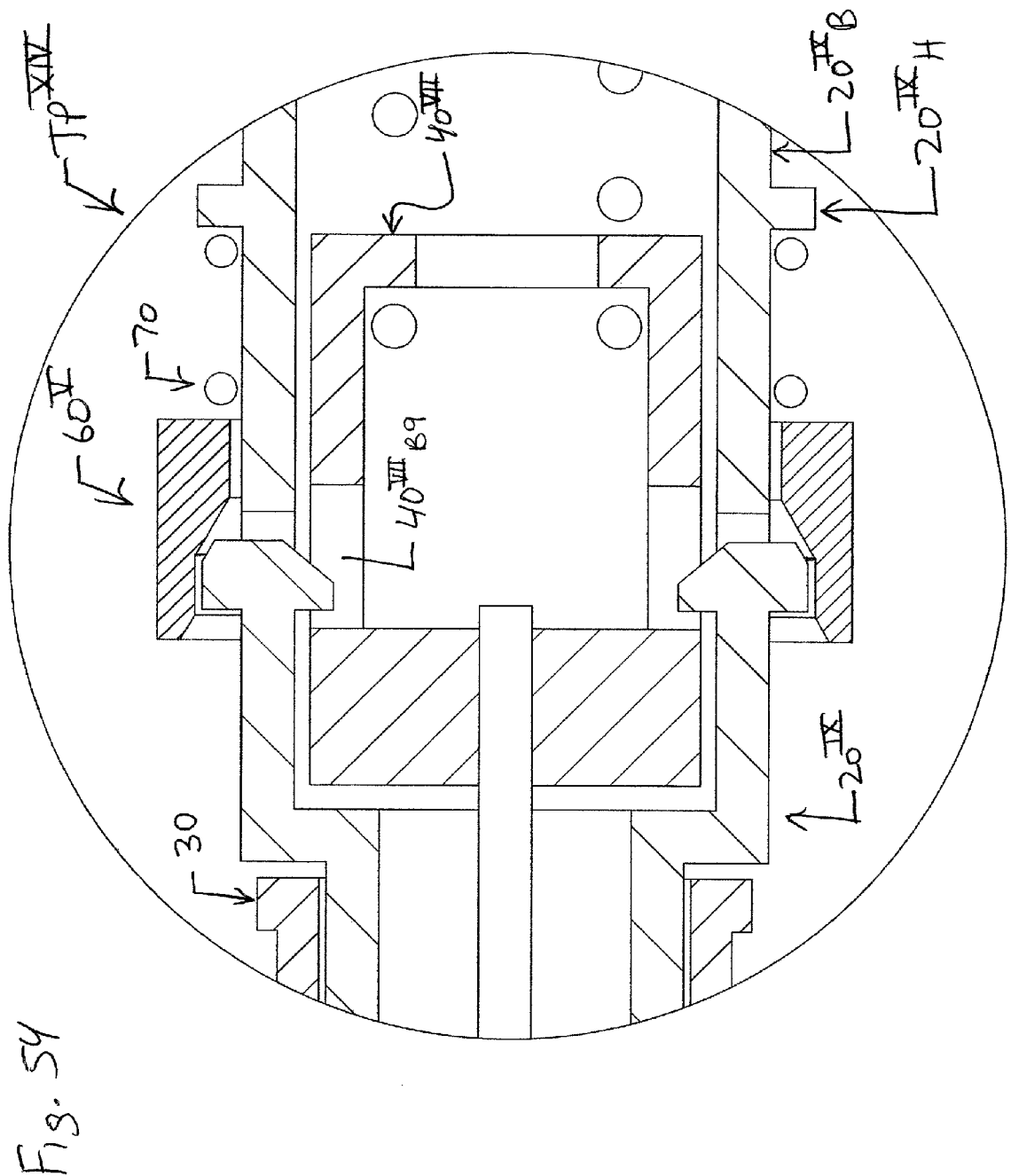
FIG. 54 shows an enlarged side cross-section view of still another non-limiting embodiment of the device. The device is shown in a ready-to-use configuration. This configuration is an injection configuration. In this embodiment, the device is triggered by axial movement of a trigger ring against the biasing force of a trigger spring. The trigger ring ensures that the deflectable retaining members of the body engage with the puncturing needle hub.
Figure 55:
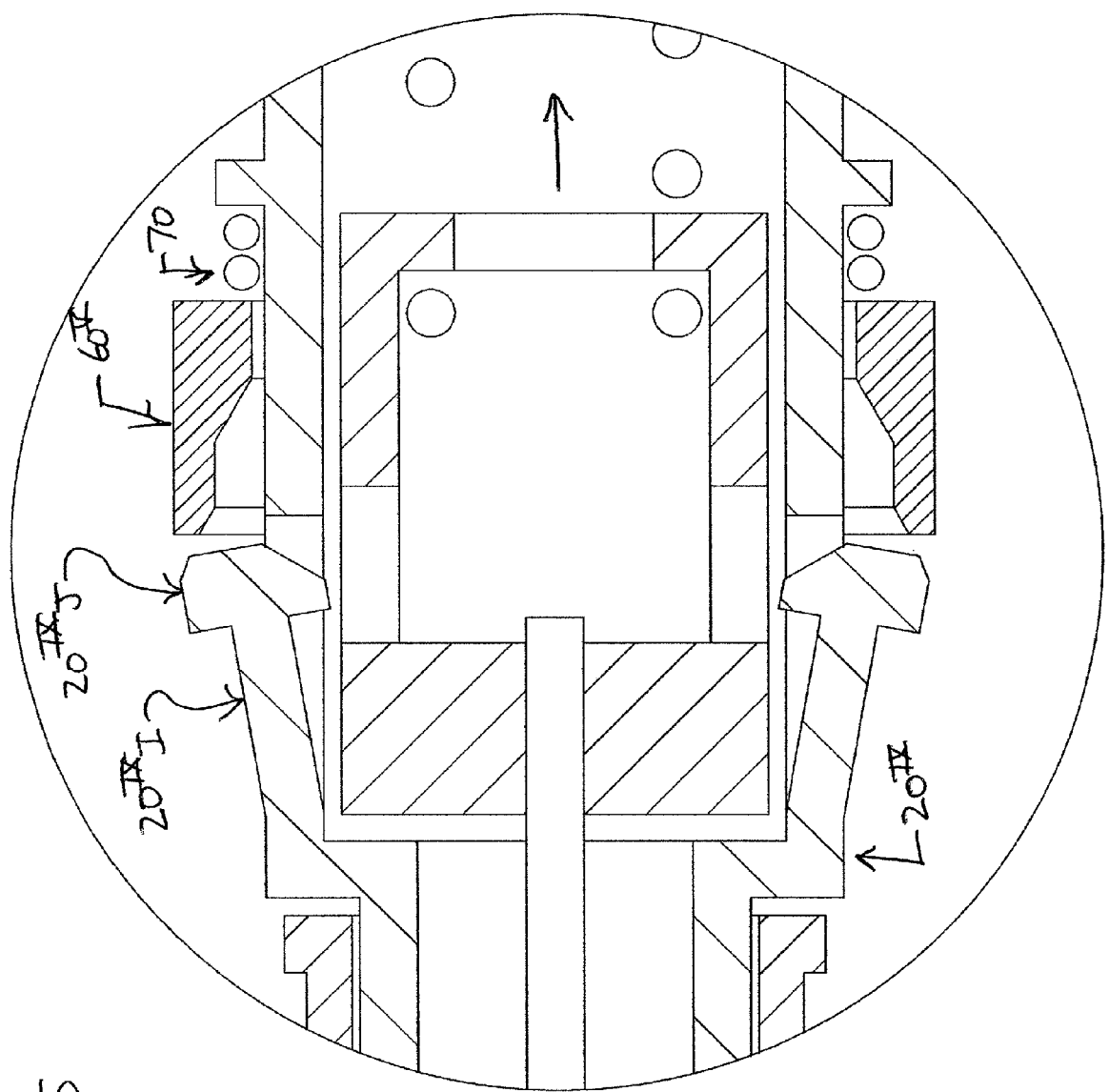
FIG. 55 shows the device of FIG. 54 during triggering. As is apparent in FIG. 55, when the trigger ring is moved back, retaining members of the body deflect outwards to a relaxed position and disengage from the puncturing needle hub which can then be moved along the direction of arrow via the spring disposed inside the body of the device.
Figure 56:
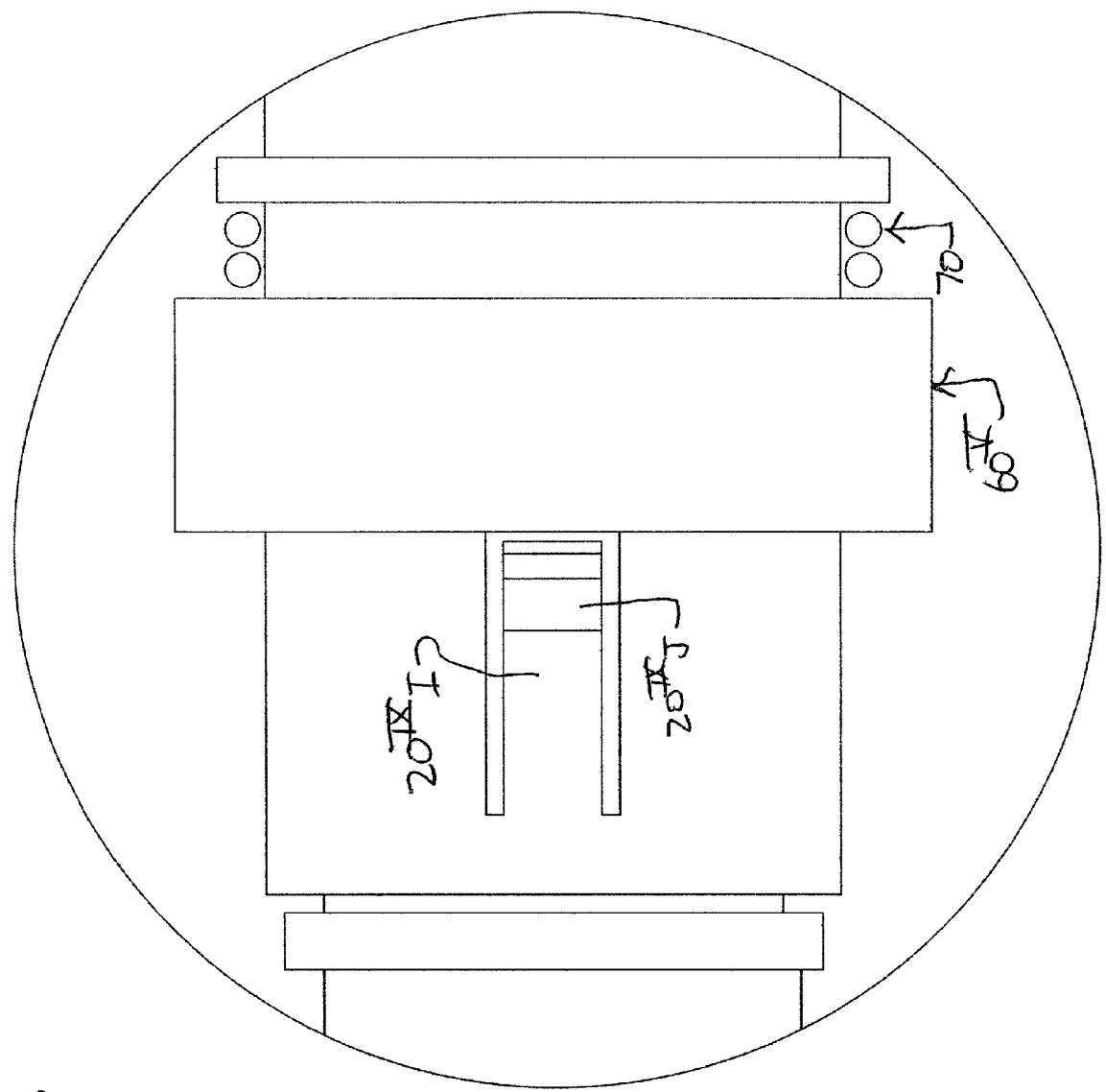
FIG. 56 shows a side view the device of FIG. 55, but rotated 90 degrees.
Figure 57:
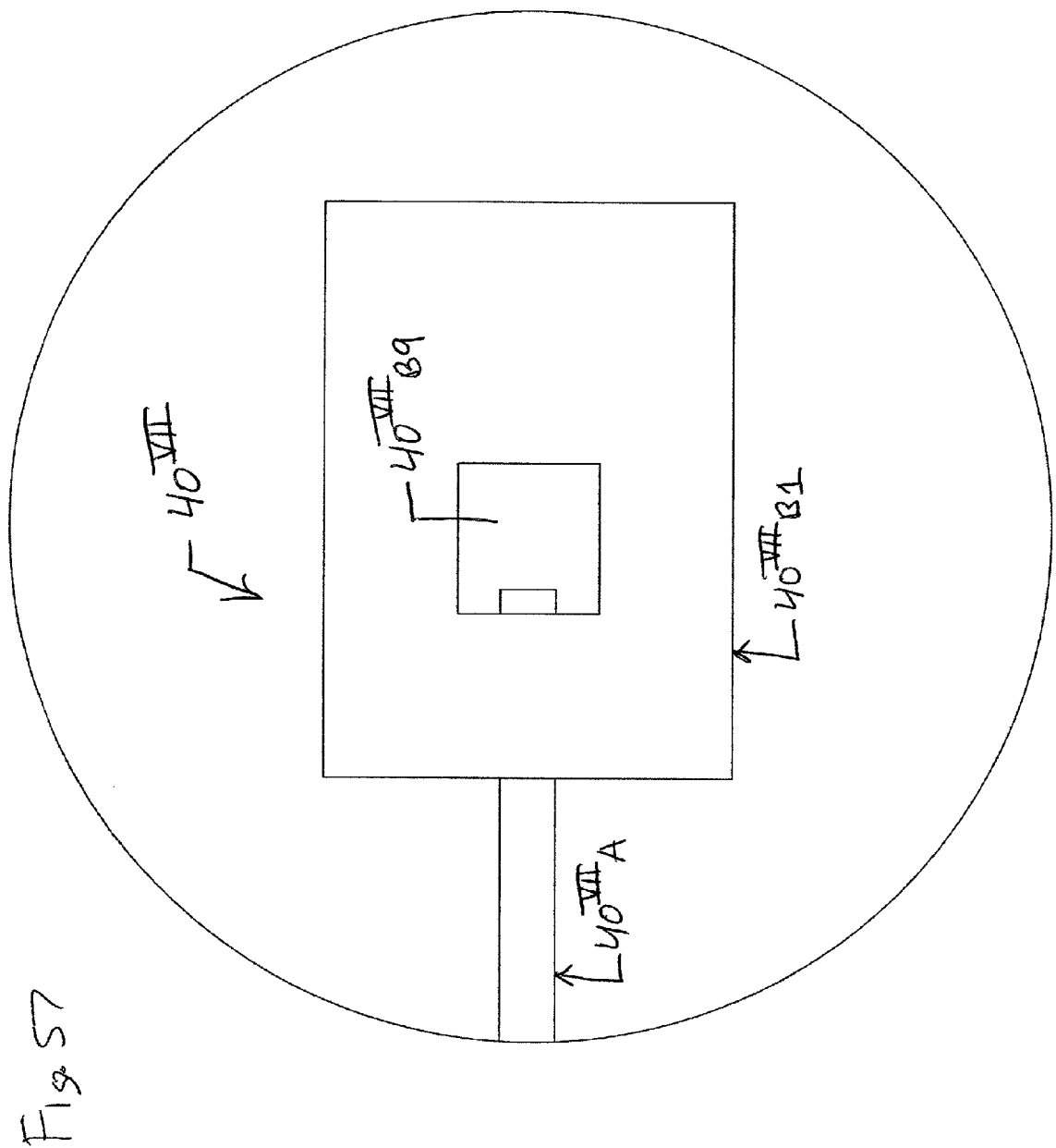
FIG. 57 shows a side view the puncturing needle/hub used in the device of FIG. 54, but rotated 90 degrees.

FIGS. 54-57 show another non-limiting embodiment of the device, which like that of FIG. 5, utilizes a cannula portion 30 and a tool portion $TP^{XIV}$. In FIG. 54, the device is shown in a ready-to-use or trigger-set configuration. This is the configuration which allows a user of the device to inject the cannula portion 30 into the skin and/or tissue. This embodiment allows a user to use axial movement of a trigger sleeve $60^V$ to cause triggering of the device. Thus, triggering occurs when the trigger ring $60^V$ is moved back against the biasing force of the a spring 70 to the point where the ring $60^V$ causes the deflectable retaining members $20^{IX}J$ of the body $20^{IX}$ to disengage from the openings $40^{VII}B9$ of the needle hub $40^{VII}$. The spring 70 is arranged axially compressed between a flange $20^{IX}H$ and the trigger ring $60^V$. To trigger the device, the user can use his or her thumb and forefinger on or in front of the trigger ring $60^V$. The user can then move the ring $60^V$ rearwards until the arms $20^{IX}I$ of the deflectable retaining members $20^{IX}J$ deflect outwardly and the deflectable retaining members $20^{IX}J$ disengage from the openings $40^{VII}B9$ of the needle hub $40^{VII}$ (see FIG. 55). As can be seen in FIG. 57, the two oppositely arranged openings $40^{VII}B9$ are arranged on the generally cylindrical portion $40^{VII}B1$ of the needle hub $40^{VII}$ and, as in previous embodiments, the needle member $40^{VII}$ includes a puncturing needle $40^{VII}A$.

Figure 58:
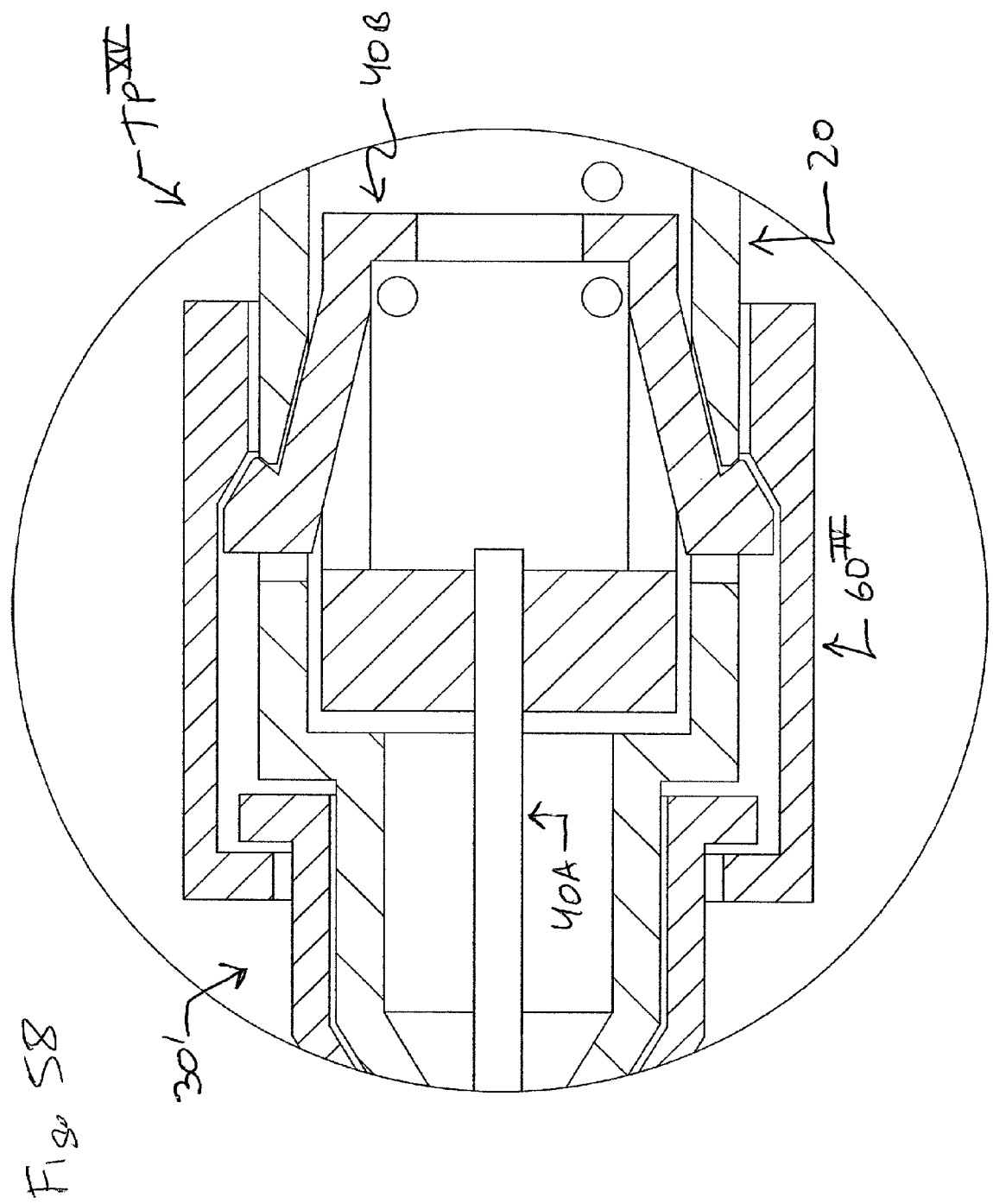
FIG. 58 shows an enlarged side cross-section view of still another non-limiting embodiment of the device. The device is similar to that of FIG. 49 except that the trigger sleeve is configured to be removed from the body of the device and/or has no flange to retain the trigger sleeve on the body.

FIG. 58 shows still another non-limiting embodiment of the device. The device is similar to that of FIG. 49 except that the trigger sleeve $60^{IV}$ is configured to be removed from the body 20 of the device and/or has no flange to retain the trigger sleeve $60^{IV}$ on the body 20.

Figure 59:
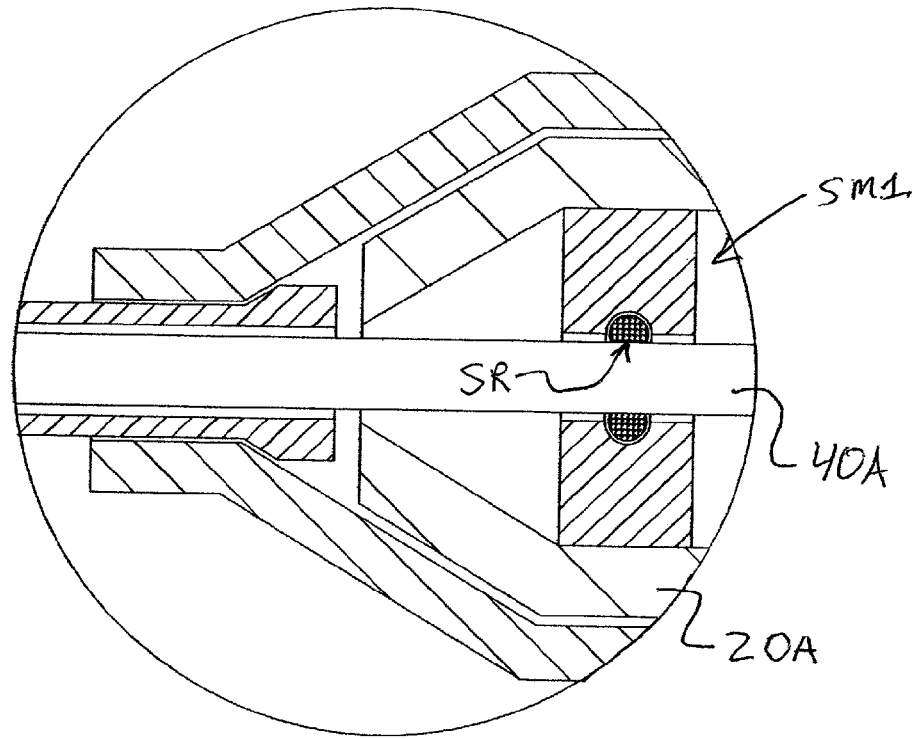
FIG. 59 shows an enlarged side cross-section view of still another non-limiting embodiment of the device. The device is similar to that of FIG. 1 except that it utilizes a sealing member to ensure that body fluid does not pass into the body of the device after triggering. A sealing ring ensures that sealing is provided between the puncturing needle and the body of the device.

FIG. 59 shows an enlarged side cross-section view of still another non-limiting embodiment of the device. The device is similar to that of FIG. 1 except that the tool portion utilizes a sealing member SM1 to ensure that body fluid(s) do not pass into the front portion 20A of the tool portion after triggering. A sealing ring SR ensures that sealing is provided between the puncturing needle 40A and the tool portion. Such an arrangement can be used on any of the herein described embodiments.

Figure 60:
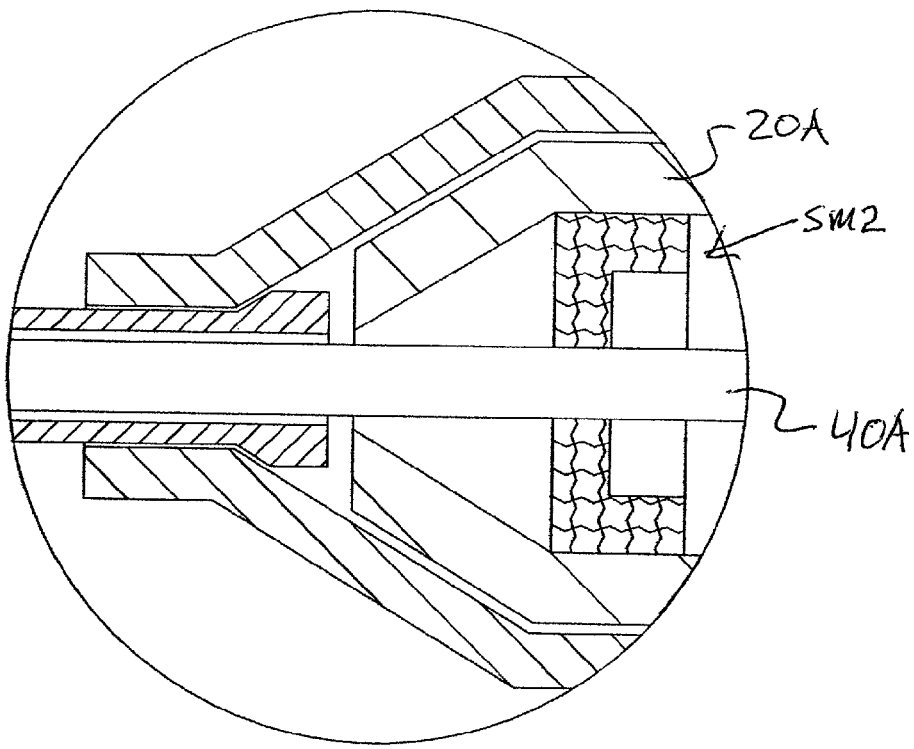
FIG. 60 shows an enlarged side cross-section view of still another non-limiting embodiment of the device. The device is similar to that of FIG. 1 except that it utilizes a resealable and puncturable sealing member to ensure that body fluid does not pass into the body of the device after triggering.

FIG. 60 shows an enlarged side cross-section view of still another non-limiting embodiment of the device. The device is similar to that of FIG. 1 except that it utilizes a resealable and puncturable sealing member SM2 to ensure that body fluid does not pass into the front portion 20A of the tool portion after triggering.

The devices described herein can also utilize one or more features disclosed in the prior art documents expressly incorporated by reference herein. The invention also contemplates using one or more features from one disclosed embodiment on one or more other disclosed embodiments. For example, the rear configuration shown in FIGS. 21-22 can be used on any of the herein disclosed embodiments. Furthermore, one or more of the various parts or features of the tool portion can preferably be made as one-piece structures by e.g., injection molding, when doing so reduces costs of manufacture. Non-limiting materials for most of the parts include synthetic resins such as those approved for syringes, blood collection devices, or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A device for installing and/or injecting a cannula comprising:
   a body comprising a cannula mounting interface;
   a needle holding member arranged in the body and being coupled to a retractable needle sized and configured to extend into a cannula when installed on the cannula mounting interface;
   a spring that is axially expanded when the device is in a ready-to-use or trigger-set configuration; and
   a triggering system comprising at least one of:
      at least one integrally formed deflectable retaining portion of the needle holding member extending into an opening arranged on a sidewall of the body and being engagable by a user's finger;
      a user engagable axially moveable member moveable between an initial position and a triggering position that causes a triggering of the device, said axially moveable member moving axially before the triggering of the device;
      a user engagable moveable member arranged on one end of the body and being moveable between an initial position and a triggering position that causes a triggering of the device, said movable member being arranged to slide over a portion of the body when in the triggering position;
      a user engagable sleeve member movably mounted to the body and being axially moveable between an initial position and a position resulting in axial compression of the spring; and
      a user engagable axially movable trigger movable between an initial position and a triggering position that causes a triggering of the device, said triggering occurring after the axially moveable trigger moves axially away from the initial position.

2. The device of claim 1, wherein the spring is structured and arranged to move the needle holding member to a retracted position within the body and further comprising a cannula hub arranged on a front end of the body, wherein the spring is arranged on a side of the needle holding member opposite the needle or the cannula.

3. The device of claim 1, further comprising a removable cannula hub arranged on a front end of the body.

4. The device of claim 1, wherein the cannula is an IV infusion cannula.

5. The device of claim 1, wherein the axially movable member comprises an axially movable trigger ring or sleeve.

6. The device of claim 1, wherein the axially movable member comprises at least a partially rotatable trigger ring or sleeve.

7. The device of claim 1, wherein the axially movable member comprises at least a partially rotatable and axially movable trigger ring or sleeve.

8. The device of claim 1, wherein the needle holding member comprises at least one deflectable retaining member releasably engaging with a portion of the body.

9. The device of claim 1, wherein the needle holding member is lockable in in a retracted position.

10. The device of claim 1, wherein the body comprises a cannula connecting interface having a luer lock type connection.

11. The device of claim 1, wherein the body comprises a connecting interface requiring rotation of a cannula to a predetermined rotational position to effect removal of the cannula from the body.

12. The device of claim 1, wherein the device has one and only one spring.

13. A device for installing and/or injecting a cannula comprising:
- a body;
- a removable cannula hub arranged on a front end of the body and comprising a insertion cannula;
- a needle holding member arranged in the body;
- a retractable needle sized and configured to extend into the insertion cannula;
- a biasing member structured and arranged to move the needle holding member to a retracted position within the body;
- the biasing member being a separate member from the needle and being axially expanded when the device is in a ready-to-use configuration; and
- an axially movable trigger that causes a triggering of the device after being contacted by a user's finger and moved axially,
- wherein the biasing member is arranged on a side of the needle holding member opposite the needle or cannula.

14. The device of claim 13, wherein the biasing member is a spring.

15. The device of claim 13, wherein the biasing member is arranged within the body between the needle holding member to a rear portion of the body.

16. The device of claim 13, wherein the trigger comprises at least one of:
- an axially movable trigger ring or sleeve;
- at least a partially rotatably movable trigger ring or sleeve; and
- at least a partially rotatable and axially movable trigger ring or sleeve.

17. A method of using the device of claim 13, the method comprising:
- injecting or insertion the cannula to a skin surface; and
- causing the needle holding member to retract into the body.

18. A method of making the device of claim 13, the method comprising:
- placing a biasing member in an expanded position inside the body; and
- connecting one end of the biasing member to the needle holding member.

19. A device for installing and/or injecting a cannula comprising:
- a body;
- a needle holding member arranged in the body;
- a retractable needle sized and configured to extend into a cannula;
- one and only one spring that is separately formed from the retractable needle,
- wherein, when the device is in a ready-to-use configuration,
    - the one and only one spring is in axially expanded state and has one end coupled to needle holding member; and
    - the retractable needle extends into the cannula.

20. A device for installing and/or injecting a cannula comprising:
- a body comprising a an integrally formed cannula mounting interface;
- a needle holding member arranged in the body;
- a retractable needle sized and configured to extend into a cannula when installed on the cannula mounting interface;
- a spring arranged within the body and being in axially expanded when the device is in a ready-to-use or trigger-set configuration; and
- a triggering system comprising at least one of:
    - an axially moveable member moveable only parallel to an axis of the body between an initial position and a triggering position that causes a triggering of the device when the axially moveable member moves axially away from the initial position;
    - a user contactable sleeve member movably mounted to the body and being axially moveable between an initial position and a triggering position resulting in axial compression of the spring; and
    - an axially movable trigger arranged to surround a portion of the body and being movable between an initial position and a triggering position that causes a triggering of the device after the axially moveable trigger moves axially away from the initial position.

21. The device of claim 20, wherein the body comprises a cannula connecting interface having a luer lock type connection.

22. The device of claim 20, wherein the device has one and only one spring.

23. A device for installing and/or injecting a cannula comprising:
- a body;
- an axially movable needle holding member arranged in the body;
- a retractable needle sized and configured to extend into a cannula;
- one and only one spring that is separately formed from the retractable needle;
- a trigger movable by a user from outside the body and being movable between an initial position and a triggering position; and
- a trigger safety structured and arranged to prevent accidental triggering,
- wherein, when the device is in a ready-to-use configuration,
    - the one and only one spring is in axially expanded state; and
    - the retractable needle extends into the cannula.

* * * * *